(12) United States Patent
Hamprecht et al.

(10) Patent No.: US 8,541,611 B2
(45) Date of Patent: Sep. 24, 2013

(54) BIFUNCTIONAL PHENYL ISO(THIO)CYANATES, PROCESSES AND INTERMEDIATES PRODUCTS FOR THEIR PREPARATION

(75) Inventors: Gerhard Hamprecht, Weinheim (DE); Michael Puhl, Lampertheim (DE); Bernd Wolf, Fuβgönheim (DE); Norbert Götz, Worms (DE); Michael Keil, Freinsheim (DE); Robert Reinhard, Ludwigshafen (DE); Ingo Sagasser, Dannstadt-Schauernheim (DE); Werner Seitz, Plankstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 13/535,544

(22) Filed: Jun. 28, 2012

(65) Prior Publication Data

US 2012/0271049 A1 Oct. 25, 2012

Related U.S. Application Data

(62) Division of application No. 12/886,986, filed on Sep. 21, 2010, now Pat. No. 8,232,421, which is a division of application No. 10/532,931, filed as application No. PCT/EP03/12013 on Oct. 29, 2003, now Pat. No. 7,820,846.

(51) Int. Cl.
 *C07C 331/28* (2006.01)
(52) U.S. Cl.
 USPC .............................................. 558/17; 558/18
(58) Field of Classification Search
 USPC .................................................... 558/17, 18
 See application file for complete search history.

(56) References Cited

U.S. PATENT DOCUMENTS

| 4,309,209 A | 1/1982 | Kobzina |
| 4,713,389 A | 12/1987 | Salzburg et al. |

FOREIGN PATENT DOCUMENTS

| EP | 0070389 A2 | 1/1983 |
| EP | 0075267 A1 | 3/1983 |
| EP | 409025 A | 1/1991 |
| WO | 0183459 A2 | 8/2001 |
| WO | 02/20531 | 3/2002 |

OTHER PUBLICATIONS

Abusov et al., "Reaction of Trifluoroacetyl Isocyanate with o-Sulfobenzimide", Bull. of the Ac. of Sci. of the USSR, Div of Chem. Sci., 39(10):2610, Part 1, 1990.
Bodrikov et al., "Adducts of nitriles with sulfur trioxide and their reactions", Zhurnal Oranicheskoi Khimii, 11(10): 2217, 1975.
Cervelló et al., "An Improved Method for the Synthesis of Sulfonylureas", Synthesis, pp. 221-222, 1990.
Encyclopedia of Chemical Technology, Fourth Edition, vol. 8, pp. 120-124.
Michurin et al., "Influence of Structural Effects on the Direction of the Reaction of Nitriles with Sulfur Trioxide", Zhurnal Organicheskoi Khimii, 13(2):432-436, J. Org. Chem USSR, 13, 1977, 390-394.
Schwenkkraus et al., "Properties and Reactions of Substituted 1,2-Thiazetidine 1,1-Dioxides: Alkylationand Acylation of 3-Haloalkyl β-Sultams and Synthesis of Bicyclic β-Sultans", Arch. Pharm., 326:437-441, 1993.
Bodrikov et al., Adducts of nitriles with sulfur troxide and their reactions; Zhurnal Organicheskoi KhimiI (1975), 11(10), 2217.

*Primary Examiner* — James O Wilson
*Assistant Examiner* — Ebenezer O Sackey
(74) *Attorney, Agent, or Firm* — Rothwell, Figg, Ernst & Manbeck, P.C.

(57) ABSTRACT

A process for preparing phenyl iso(thio)cyanates of the formula I in which a compound of the formula II or its HCl adduct is reacted with a phosgenating agent

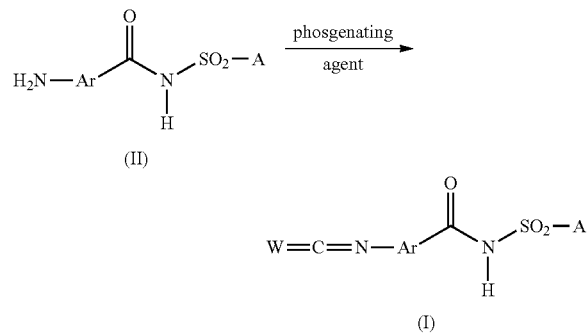

where W is oxygen or sulfur and Ar and A are as defined in claim 1 is described.
Moreover, the invention relates to the use of the phenyl iso(thio)cyanates for preparing crop protection agents.

14 Claims, No Drawings

BIFUNCTIONAL PHENYL ISO(THIO)CYANATES, PROCESSES AND INTERMEDIATES PRODUCTS FOR THEIR PREPARATION

This application is a divisional of U.S. Ser. No. 12/886,986, filed Sep. 21, 2010, which is a divisional of U.S. Ser. No. 10/532,931, filed Apr. 28, 2005, now U.S. Pat. No. 7,820,846 issued Oct. 26, 2010, which is a 35 USC §371 National Phase Entry Application from PCT/EP03/012013, filed Oct. 29, 2003, and designating the United States, which claims the benefit of German Patent Application No. 102 50 614.0 filed Oct. 30, 2002 the disclosures of which are incorporated herein in their entirety by reference.

The invention relates to a process for preparing bifunctional phenyl iso(thio)cyanates of the formula I having an acylsulfonamide group

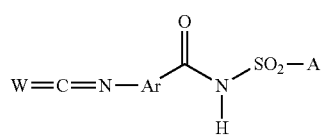

where the Variables are as defined below:
W is oxygen or sulfur,
Ar is phenyl which may be mono- or polysubstituted by the following groups: hydrogen, halogen, $C_1$-$C_4$-haloalkyl or cyano,
A is a radical derived from a primary or secondary amine or is $NH_2$,
by reacting anilines or their hydrochlorides with phosgene derivatives. The invention also relates to bifunctional phenyl iso(thio)cyanates.

Iso(thio)cyanatobenzoylsulfamic acid amides are potential precursors for the preparation of crop protection agents having a triazole-3,5-dion-4-yl group, pyrimidine-2,6-dion-1-yl group or 1,3,5-triazine-2,4,6-trion-1-yl group or their S analogs as described, for example, in WO 01/83459. Owing to their reactivity, it should be easy to convert the iso(thio)cyanato structural unit into other groups such as (thio)urea or urethane groups. However, for the reasons mentioned below, their preparation was thought to be impossible.

In principle, phenyl iso(thio)cyanates can be prepared by reacting primary aromatic amines with phosgene and thiophosgene, respectively (see, for example, Houben-Weyl, Methoden der organischen Chemie [methods of organic chemistry], 4th edition, Vol. IX, pp. 869, 875-877 and Vol. VIII, pp. 120-124). Further general processes are known, for example, from EP 70389, EP 75267 and EP 409 025.

Common to all of the processes described is that the phenyl iso(thio)cyanates used do not carry an acylsulfonamide group. This is because it is known that an iso(thio)cyanato group can react with a sulfonamide group with formation of sulfonylureas. Thus, for example, J. Cervello and T. Sastre describe, in Synthesis 1990, 221-222, the reaction of a sulfonamide with isocyanates according to the equation below:

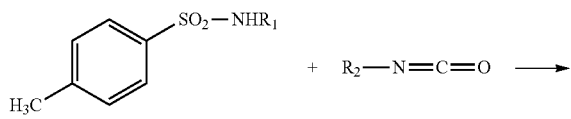

$R_1$ = H, $CH_3$
$R_2$ = aryl, alkyl

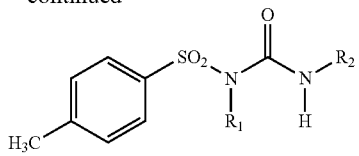

U.S. Pat. No. 4,309,209 discloses that phenyl isocyanates react with chloromethane-(N-methyl)sulfonamide (=$ClCH_2SO_2NHCH_3$) with formation of a 1,2,4-thiadiazolidine-1,1,3-trione. P. Schwenkkraus and H.-H. Otto describe, in Arch. Pharm. (Weinheim), 326 (1993), 437-441, the reaction of 3-haloalkyl-β-sultames with phenyl isocyanate with formation of carbamoyl compounds.

DE 3433391 discloses the reaction of saccharin with acyl isocyanates to give N-acylated saccharin derivatives.

In JZV Akad Nauk SSSR, Ser Khim 1990, 2874 (English translation: Bulletin of the Academy of Sciences of the USSR, Division of Chemical Sciences, Vol. 39, (1990), p. 2610), B. A. Arbuzov, N. N. Zobova and N. R. Fedotava describe the N- and O-acylation of saccharin by reaction with a trifluoroacetyl isocyanate.

Against this background, both the preparation of phenyl iso(thio)cyanates which, in the same molecule, also carry a reactive acylsulfonamide function and their isolation—without subsequent intermolecular reactions—have been thought to be impossible. A person skilled in the art would have assumed that, owing to their acidic proton, sulfonamides would react with phenyl iso(thio)cyanates to give sulfonylurea derivatives. Hitherto, no process for the preparation of phenyl iso(thio)cyanates which, as further functional group, carry an acylsulfonamide group has been described.

It is an object of the present invention to provide iso(thio)cyanatobenzoylsulfamic acid amides of the formula I.

We have found that this object is achieved, surprisingly, by a process in which an aminobenzoylsulfamic acid amide of the formula II

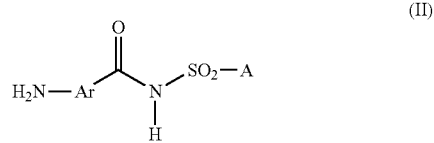

where the variables Ar and A are as defined above is reacted with phosgene, diphosgene or thiophosgene.

Accordingly, the present invention relates to a process for preparing phenyl iso(thio)cyanates of the formula I which comprises reacting a compound of the formula II or its HCl adduct with phosgene, thiophosgene or diphosgene (see Scheme 1). In Scheme 1, the variables Ar, A and W are as defined above.

Scheme 1:

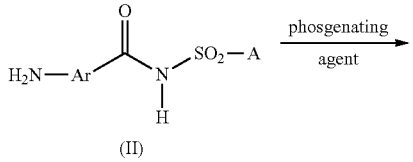

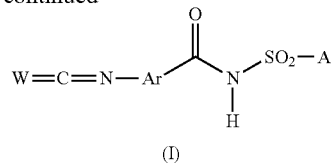

(I)

The phenyl iso(thio)cyanates I obtainable in high yield by the process according to the invention are useful intermediates for the preparation of crop protection agents, in particular of 3-(thiazolidinone)-substituted phenylsulfamoylcarboxamides. Accordingly, the present invention also provides a process for preparing 3-heterocyclyl-substituted phenylsulfamoylcarboxamides starting with phenyl iso(thio)cyanates I. Contrary to expectation, the compounds I according to the invention are stable compounds which are readily prepared, even on an industrial scale. Accordingly, the invention also relates to the phenyl iso(thio)cyanates of the formula I. The stability of the compounds I according to the invention is surprising, since a person skilled in the art would have expected an intermolecular reaction between the iso(thio)cyanato structural unit and the sulfamide grouping to take place.

The organic molecular moieties mentioned in the definition of the substituents are—like the term halogen—collective terms for individual enumerations of the individual group members, where the term $C_n$-$C_m$ indicates the possible number of carbon atoms in the molecular moiety. All carbon chains, i.e. all alkyl, alkenyl and alkynyl moieties, may be straight-chain or branched. Unless indicated otherwise, halogenated substituents preferably carry one to six identical or different halogen atoms. In each case, the term "halogen" denotes fluorine, chlorine, bromine or iodine.

Examples of other meanings are:

$C_1$-$C_4$-alkyl: for example methyl, ethyl, propyl, 1-methylethyl, butyl, 1-methylpropyl, 2-methylpropyl or 1,1-dimethylethyl;

$C_1$-$C_{10}$-alkyl: a saturated aliphatic hydrocarbon radical having 1 to 10 carbon atoms, for example $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl, 1-ethyl-3-methylpropyl, n-heptyl, n-nonyl, n-decyl, 1-methylhexyl, 1-ethylhexyl, 1-methylheptyl, 1-methyloctyl, 1-methylnonyl;

$C_2$-$C_{10}$-alkenyl: a monounsaturated olefinic hydrocarbon radical having 2 to 10 carbon atoms, preferably 3 to 6 carbon atoms, for example ethenyl, prop-2-en-1-yl (=allyl), prop-1-en-1-yl, but-1-en-4-yl, but-2-en-1-yl, but-3-en-1-yl, 1-methylprop-2-en-1-yl, 2-methylprop-2-en-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, 1-ethylprop-1-en-2-yl, n-hex-1-en-1-yl, n-hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-2-en-1-yl, hept-2-en-1-yl, oct-2-en-1-yl, non-2-en-1-yl, dec-2-en-1-yl;

$C_2$-$C_{10}$-alkynyl: a hydrocarbon radical having 2 to 10 carbon atoms, preferably 3 to 6 carbon atoms, and one triple bond, for example ethynyl, prop-2-yn-1-yl (=propargyl), prop-1-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl, 4-methylpent-2-yn-5-yl, hept-2-yn-1-yl, Oct-2-yn-1-yl, non-2-yn-1-yl, dec-2-yn-1-yl;

$C_1$-$C_4$-haloalkyl: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$-$C_{10}$-haloalkyl: $C_1$-$C_{10}$-alkyl as mentioned above in which 1 to 6 hydrogen atoms are substituted by halogen atoms, preferably by fluorine and/or chlorine, for example: $C_1$-$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl or 6-iodohexyl;

$C_2$-$C_{10}$-haloalkenyl: $C_2$-$C_{10}$-alkenyl as mentioned above in which 1 to 6 hydrogen atoms are substituted by halogen atoms, preferably by fluorine and/or chlorine: for example 2-chloroallyl, 3-chloroallyl, 2,3-dichloroallyl, 3,3-dichloroallyl, 2,3,3-trichloroallyl, 2,3-dichlorobut-2-en-1-yl, 2-bromoallyl, 3-bromoallyl, 2,3-dibromoallyl, 3,3-dibromoallyl, 2,3,3-tribromoallyl or 2,3-dibromobut-2-en-1-yl;

$C_2$-$C_{10}$-haloalkynyl: $C_2$-$C_{10}$-alkynyl as mentioned above in which 1 to 6 hydrogen atoms are substituted by halogen atoms, preferably by fluorine and/or chlorine: for example 1,1-difluoroprop-2-yn-1-yl, 1,1-difluorobut-2- yn-1-yl, 4-fluorobut-2-yn-1-yl, 4-chlorobut-2-yn-1-yl, 5-fluoropent-3-yn-1-yl or 6-fluorohex-4-yn-1-yl;

$C_1$-$C_{10}$-cyanoalkyl: $C_1$-$C_{10}$-alkyl substituted by a CN group, for example cyanomethyl, 1-cyanoethyl, 2-cyanoethyl, 1-cyanopropyl, 2-cyanopropyl, 3-cyanopropyl, 1-cyanoprop-2-yl, 2-cyanoprop-2-yl, 1-cyanobutyl, 2-cyanobutyl, 3-cyanobutyl, 4-cyanobutyl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, 3-cyano-2,2-dimethylpropyl, 6-cyanohex-1-yl, 7-cyanohept-1-yl, 8-cyanooct-1-yl, 9-cyanonon-1-yl, 10-cyanodec-1-yl;

$C_3$-$C_{10}$-cycloalkyl: a cycloaliphatic radical having 3 to 10 carbon atoms: for example cyclopropyl, cyclobutyl, cyclopentyl, cyclohexyl, cycloheptyl, cyclooctyl, cyclononyl or cyclodecyl;

$C_3$-$C_{10}$-cycloalkenyl: a cycloaliphatic radical having 3 to 10 carbon atoms and a double bond: for example cyclopropen-1-yl, cyclobuten-1-yl, cyclopenten-1-yl, cyclohexen-1-yl, cyclohepten-1-yl, cycloocten-1-yl, cyclononen-1-yl, cyclodecen-1-yl, cyclopent-2-en-1-yl, cyclohex-2-en-1-yl, cyclohept-2-en-1-yl, cyclooct-2-en-1-yl, cyclonon-2-en-1-yl, cyclodec-2-en-1-yl, cyclohex-3-en-1-yl, cyclohept-3-en-1-yl, cyclooct-3-en-1-yl, cyclooct-4-en-1-yl, cyclonon-3-en-1-yl, cyclonon-4-en-1-yl, cyclodec-4-en-1-yl or cyclodec-3-en-1-yl;

$C_1$-$C_4$-alkylcarbonyl: an alkyl radical having 1 to 4 carbon atoms which is attached via a carbonyl group, for example acetyl, propionyl, butyryl or isobutyryl;

($C_1$-$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

di-($C_1$-$C_4$-alkyl)aminocarbonyl: for example N,N-dimethylaminocarbonyl, N,N-diethylaminocarbonyl, N,N-di-(1-methylethyl)aminocarbonyl, N,N-dipropylaminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

$C_1$-$C_4$-alkoxy: an alkyl radical having 1 to 4 carbon atoms which is attached via an oxygen atom, for example methoxy, ethoxy, propoxy, 1-methylethoxy, butoxy, 1-methylpropoxy, 2-methylpropoxy or 1,1-dimethylethoxy;

$C_1$-$C_4$-alkoxycarbonyl: an alkoxy radical having 1 to 4 carbon atoms which is attached via a carbonyl group, for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$-$C_4$-alkylthio($C_1$-$C_4$-alkylsulfanyl: $C_1$-$C_4$-alkyl-S—): an alkyl radical having 1 to 4 carbon atoms which is attached via a sulfur atom, for example methylthio, ethylthio, propylthio, 1-methylethylthio, butylthio, 1-methylpropylthio, 2-methylpropylthio or 1,1-dimethylethylthio;

$C_1$-$C_4$-alkylsulfinyl($C_1$-$C_4$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$-$C_4$-alkylsulfonyl($C_1$-$C_4$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl;

3- to 8-membered heterocyclyl: a heterocyclic radical which has 3, 4, 5, 6, 7 or 8 ring members, 1, 2 or 3 of the ring members being heteroatoms selected from the group consisting of oxygen, sulfur, nitrogen and a group $NR^6$ (where $R^6$ is hydrogen, $C_1$-$C_6$-alkyl, $C_3$-$C_6$-alkenyl or $C_3$-$C_6$-alkynyl). Moreover, the heterocycle may optionally have one or two carbonyl groups or thiocarbonyl groups as ring members. The heterocycle may be aromatic (heteroaryl) or partially or fully saturated.

Examples of saturated heterocycles are:

oxiran-1-yl, aziridin-1-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4- yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-4-yl, 1,3-dithiepan-5-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl;

examples of unsaturated heterocycles are:
dihydrofuran-2-yl, 1,2-oxazolin-3-yl, 1,2-oxazolin-5-yl, 1,3-oxazolin-2-yl;

examples of aromatic heterocyclyl are the 5- and 6-membered aromatic heterocyclic radicals, for example furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, furanyl and thienyl.

The radical A, which is derived from a primary or secondary amine, is generally a group of the formula —NR$^1$R$^2$, where the variables R$^1$ and R$^2$ are as defined below:

R$^1$ and R$^2$ independently of one another represent hydrogen, $C_1$-$C_{10}$-alkyl, $C_2$-$C_{10}$-alkenyl or $C_2$-$C_{10}$-alkynyl which may be unsubstituted or substituted by one of the following radicals: $C_1$-$C_4$-alkoxy, $C_1$-$C_4$-alkylthio, CN, NO$_2$, formyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl, $C_1$-$C_4$-alkylsulfinyl, $C_1$-$C_4$-alkylsulfonyl, $C_3$-$C_{10}$-cycloalkyl, 3- to 8-membered heterocyclyl having one, two or three heteroatoms selected from the group consisting of O, S, N and a group NR$^6$ (where R$^6$ is hydrogen, $C_1$-$C_8$-alkyl, $C_3$-$C_6$-alkenyl or $C_3$-$C_8$-alkynyl), phenyl, which for its part may have 1, 2, 3 or 4 substituents selected from the group consisting of halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, $C_1$-$C_3$-alkylamino, $C_1$-$C_3$-dialkylamino, formyl, nitro and cyano, $C_1$-$C_{10}$-haloalkyl, $C_2$-$C_{10}$-haloalkenyl, $C_2$-$C_{10}$-haloalkynyl, $C_3$-$C_8$-cycloalkyl, $C_3$-$C_{10}$-cycloalkenyl, 3- to 8-membered heterocyclyl having one to three heteroatoms selected from the group consisting of O, S, N and a group NR$^6$ (where R$^6$ is hydrogen, $C_1$-$C_8$-alkyl, $C_3$-$C_6$-alkenyl or $C_3$-$C_6$-alkynyl), phenyl or naphthyl, where $C_3$-$C_8$-cycloalkyl, $C_3$-$C_{10}$-cycloalkenyl, 3-to 8-membered heterocyclyl, phenyl and naphthyl may for their part have 1, 2, 3 or 4 substituents selected from the group consisting of halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, $C_1$-$C_3$-alkylamino, $C_1$-$C_3$-dialkylamino, phenoxy, nitro and cyano, or R$^1$ and R$^2$ together form a saturated or partially unsaturated 5- to 8-membered nitrogen heterocycle which for its part may be substituted by $C_1$-$C_4$-alkyl, $C_1$-$C_4$-alkoxy and/or $C_1$-$C_4$-haloalkyl and may have one or two carbonyl groups, thiocarbonyl groups and/or one or two further heteroatoms selected from the group consisting of O, S, N and a group NR$^6$ (where R$^6$ is as defined above) as ring members.

Preferred substituents R$^1$ and R$^2$ are, independently of one another, selected from the group consisting of hydrogen, $C_1$-$C_6$-alkyl, which is unsubstituted or substituted by a substituent selected from the group consisting of halogen, cyano, $C_1$-$C_4$-alkoxy, $C_1$-$C_4$-alkoxycarbonyl, $C_1$-$C_4$-alkylthio, $C_3$-$C_8$-cycloalkyl, phenyl, which for its part is unsubstituted or substituted by halogen or $C_1$-$C_4$-alkoxy, furyl, thienyl, 1,3-dioxolanyl. Preference is furthermore given to $C_2$-$C_6$-alkenyl, $C_2$-$C_6$-alkynyl, $C_3$-$C_8$-cycloalkyl or phenyl, which is unsubstituted or substituted by 1 or 2 substituents selected from the group consisting of halogen, $C_1$-$C_4$-alkyl, $C_1$-$C_4$-fluoroalkyl, $C_1$-$C_4$-alkoxy, $C_1$-$C_4$-alkoxycarbonyl, nitro and $C_1$-$C_3$-dialkylamino, naphthtyl or pyridyl. In a further preferred embodiment, R$^1$ and R$^2$ together form a five-, six- or seven-membered saturated or unsaturated nitrogen heterocycle which may contain a further heteroatom selected from the group consisting of N, a group NR$^6$ (where R$^6$ is as defined above) and O as ring member and/or may be substituted by one, two or three substituents selected from the group consisting of $C_1$-$C_4$-alkyl and $C_1$-$C_4$-haloalkyl.

In particularly preferred embodiment of the invention, one of the radicals R$^1$ or R$^2$ is hydrogen, $C_1$-$C_6$-alkyl, $C_2$-$C_6$-alkenyl or $C_2$-$C_6$-alkynyl and the other radical R$^1$ or R$^2$ is $C_1$-$C_6$-alkyl, $C_3$-$C_8$-cycloalkyl or phenyl.

The group Ar is in particular a group of the formula Ar-1

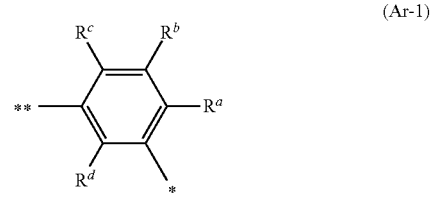

(Ar-1)

where

R$^a$, R$^b$, R$^c$ and R$^d$ independently of one another are hydrogen, halogen, $C_1$-$C_4$-haloalkyl or cyano;

* denotes the point of attachment of Ar to the C(O) group and

** denotes the point of attachment of Ar to the nitrogen atom of the amino, nitro or iso(thio)cyanato group.

In a particularly preferred embodiment of the invention, the variables R$^a$, R$^b$, R$^c$ and R$^d$ are as defined below, in each case on their own or in combination:

R$^a$ is halogen or cyano, in particular fluorine, chlorine or cyano;

R$^b$ is hydrogen;

R$^c$ is halogen or hydrogen, in particular fluorine, chlorine or hydrogen;

R$^d$ is hydrogen.

Accordingly, the present invention relates in particular to the preparation of the compounds IA,

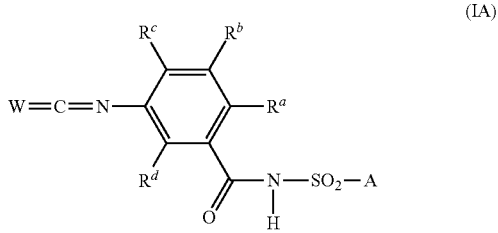

(IA)

where the variables $R^a$, $R^b$, $R^c$, $R^d$, A and W are as defined above.

In particular, the present invention relates to the preparation of the compounds IA.1 where A is $NR^1R^2$. Hereinbelow, these compounds are referred to as compounds IA.1.

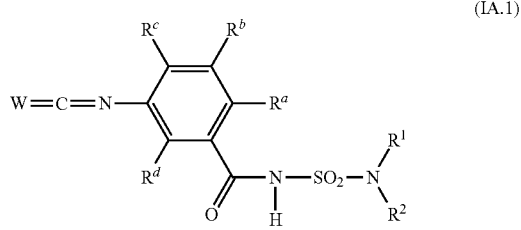

(IA.1)

The reaction of the compound II with phosgene, thiophosgene or diphosgene, hereinbelow also referred to as phosgenating agent, is usually carried out in an inert organic solvent. Suitable solvents for these reactions are—depending on the temperature range—hydrocarbons, such as pentane, hexane, cyclopentane, cyclohexane, toluene, xylene; chlorinated hydrocarbons, such as methylene chloride, chloroform, 1,2-dichloroethane, 1,1,2,2-tetrachloroethane, chlorobenzene, 1,2-, 1,3- or 1,4-dichlorobenzene, ethers, such as 1,4-dioxane, anisole; glycol ethers, such as dimethyl glycol ether, diethyl glycol ether, diethylene glycol dimethyl ether; esters, such as ethyl acetate, propyl acetate, methyl isobutyrate, isobutyl acetate; carboxamides, such as N,N-dimethylformamide, N-methylpyrrolidone; nitrated hydrocarbons, such as nitrobenzene; tetraalkylureas such as tetraethylurea, tetrabutylurea, dimethylethyleneurea, dimethylpropyleneurea; nitriles, such as acetonitrile, propionitrile, butyronitrile or isobutyronitrile; or else mixtures of individual solvents.

If phosgene is used, preference is given to using a solvent which is substantially free of protic impurities such as water and alcohols. However, in the preparation of the isothiocyanates, it is also possible, similarly to Houben-Weyl, Methoden der organischen Chemie, 4th edition, Vol. IX, p. 875, to carry out the reaction of II with thiophosgene in a two-phase system comprising water and a water-immiscible organic solvent, or else in water.

In general, the compound II is initially charged in a reaction vessel, preferably as a solution or suspension in one of the solvents mentioned above, and the phosgenating agent is then added. The addition of the phosgenating agent is preferably carried out with stirring. The addition preferably takes place over a period of from 10 to 60 minutes. The phosgenating agent can be added as such or as a solution in one of the solvents mentioned above. In the case of phosgene, this is generally introduced into the solution or suspension.

The reaction temperature will generally not exceed 180° C., preferably 120° C. and in particular 100° C., and will generally be at least 40° C. and preferably at least 50° C. Frequently, at least the major part of the phosgenating agent will be added at a low temperature, for example in the range from 0 to 40° C., in particular from 10 to 40° C. and especially from 20 to 30° C., and the mixture will be heated during or after the addition to a temperature in the range from 40 to 180° C., in particular from 50 to 120° C. and especially from 70 to 100° C., until the reaction has gone to completion.

In general, from 0.9 to 2, preferably from 0.95 to 1.5, with particular preference from 0.98 to 1.09, molar equivalents of phosgenating agent are employed per mole of the compound II.

If appropriate, the conversion of II is carried out in the presence of a base. Suitable bases are, for example, basic inorganic compounds, for example alkali metal or alkaline earth metal hydroxides, bicarbonates or carbonates. However, the reaction can also be carried out in the presence of an organic base, for example a tertiary amine, such as triethylamine, tri-n-propylamine, N-ethyldiisopropylamine, pyridine, α-, β-, γ-picoline, 2,4-, 2,6-lutidine, N-methylpyrrolidine, dimethylaniline, N,N-dimethylcyclohexylamine, quinoline or acridine. The base (calculated as base equivalent) can be employed in substoichiometric, superstoichiometric or equimolar amounts, based on the compound II. In general, from 0.01 to 6 mol, preferably from 0.1 to 3 mol, of base are employed per mole of the compound II.

In another embodiment of the process according to the invention, the reaction is carried out in the presence of hydrogen chloride. In this case, the amount of hydrogen chloride is usually from 0.9 to 5.0 mol, preferably from 1.0 to 2.5 mol and in particular from 1.0 to 1.2 mol, of hydrogen chloride per mole of the compound II. The procedure usually adopted here is that the above-mentioned amount of gaseous hydrogen chloride is initially introduced into or a solution of hydrogen chloride in a solvent is initially added to a solution or suspension of the compound II in one of the abovementioned solvents, the phosgenating agent is then added in the manner described above and the reaction is then continued in the manner described above. The introduction of hydrogen chloride is usually carried out at temperatures from 10° C. to 60° C., preferably from 20° C. to 30° C.

If the process is carried out in the presence of hydrogen chloride, it is possible to use activated carbon as the catalyst. The amount of activated carbon is expediently from 1 to 10% by weight, preferably from 1 to 3% by weight, based on the weight of the compound II.

The reaction can be carried out at atmospheric pressure or under superatmospheric pressure, continuously or batchwise. In general, the reaction of the compound II with a phosgenating agent will be carried out with exclusion of water. If appropriate, it may be advantageous to carry out the reaction under a protective atmosphere.

Work-up to isolate the target product can be carried out using the methods customary for this purpose. If the phosgenating agent used is phosgene, in general unreacted phosgene will initially be removed, for example by introducing a stream of nitrogen into the reaction mixture. The solvent is then removed by customary processes, for example by distillation. For further purification, it is possible to employ processes such as crystallization or chromatography, for example on silica gel. If appropriate, the residue can also be purified by trituration with a solvent, for example an aromatic hydrocarbon, such as benzene, toluene or xylene, or an aliphatic hydrocarbon, such as petroleum ether, hexane, cyclohexane, pentane, an ether, such as diethyl ether, etc., and mixtures of these.

The compounds of the formula II required as starting materials for carrying out the process according to the invention are likewise novel and, as interesting precursors, of importance for the process according to the invention. In the formula II, the variables Ar and A preferably denote those radicals which have already been mentioned in connection with the description of the compounds I according to the invention as being preferred for these substituents.

The compounds of the formula II can be obtained analogously to known processes for preparing anilines. The aniline compounds of the formula II can be prepared, for example, in accordance with Scheme 2 by initially reacting an aroyl compound of the formula III with a sulfamic acid amide IV in a condensation reaction to give an N-aroylsulfamic acid amide of the formula V, followed by reduction of the resulting N-aroylsulfamic acid amide V to give the compound II.

Scheme 2:

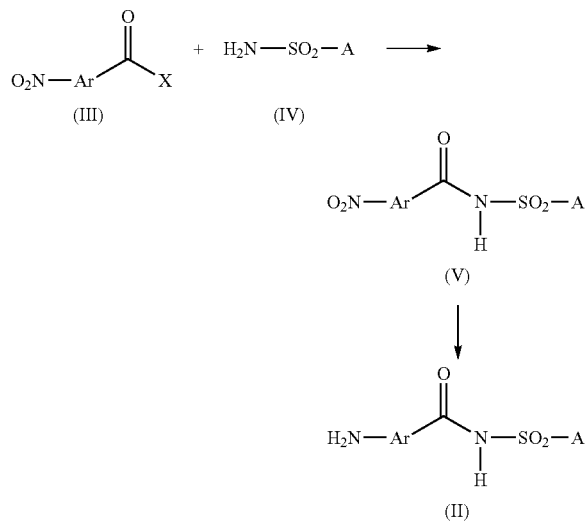

In Scheme 2, the variables A and Ar have the meanings given above, in particular the meanings given as being preferred. X is halogen, preferably chlorine, hydroxyl or a $C_1$-$C_4$-alkoxy group. The condensation of aroyl compounds of the formula III with sulfamic acid amides of the formula IV to give the corresponding benzoylsulfamides of the formula V is carried out similarly to known processes, for example as described in WO 01/83459, pp. 31-35, in the not yet published German patent application DE 102 21 910.0, the disclosure of which is hereby incorporated by way of reference.

The first reaction step is illustrated in more detail below:

If X in the formula III is hydroxyl, the carboxylic acid III is preferably initially activated by reaction with a coupling agent. The activated carboxylic acid III is then, generally without prior isolation, reacted with the sulfamic acid amide IV. Suitable coupling agents are, for example, N,N'-carbonyldiimidazole or carbodiimides, such as dicyclohexylcarbodiimide. These are generally employed in at least equimolar amount and up to a four-fold excess, based on the carboxylic acid III. If appropriate, the resulting reaction mixture of carboxylic acid III and coupling agent is heated and then allowed to cool to room temperature. The reaction is usually carried out in a solvent. Suitable solvents are, for example, chlorinated hydrocarbons, such as methylene chloride, 1,2-dichloroethane; ethers, for example dialkyl ethers, such as diethyl ether or methyl tert-butyl ether, or cyclic ethers, such as tetrahydrofuran or dioxane; carboxamides, such as dimethylformamide; N-methyllactams, such as N-methylpyrrolidone; nitriles, such as acetonitrile; aromatic hydrocarbons, such as toluene; aromatic amines, such as pyridine; or mixtures of these. This is followed by addition of the sulfamic acid amide IV. In general, the sulfamide IV is dissolved in the same solvent that is used for activating the carboxylic acid.

If X in the formula III is $C_1$-$C_4$-alkoxy, the esters can initially be converted according to known processes by hydrolysis in an acidic medium using strong mineral acids, such as concentrated hydrochloric acid or sulfuric acid, or organic acids, such as glacial acetic acid, or mixtures of these, into the corresponding carboxylic acids III. Alternatively, esters can also be hydrolyzed under alkaline conditions using bases such as alkali metal hydroxide, for example sodium hydroxide or potassium hydroxide, in the presence of water.

The carboxylic acids III (X=OH) can then be reacted in the manner described above or initially be converted into the acid chlorides (X=Cl) using a chlorinating agent, such as thionyl chloride or phosgene, followed by reaction of the acid chlorides with IV in the manner described below. The acid chlorides are prepared similarly to known processes, for example as described in EP 1 176 133 and WO 01/087872.

However, it is also possible to react the carboxylic acid ester of the formula III in which X is $C_1$-$C_4$-alkoxy directly with a sulfamic acid amide IV or a metal salt thereof in an amidation reaction with cleavage of the ester radical. The reaction is carried out similarly to the procedure described in Houben-Weyl, 4th edition, Vol. VIII, pp. 658-659.

If X in formula III is halogen, the aroyl compound III, preferably diluted in an inert solvent, will generally be added to the sulfamic acid amide of the formula IV, preferably likewise diluted in an inert solvent. It is, of course, also possible to initially charge the aroyl compound III and to add the sulfamic acid amide IV.

The molar ratios in which the starting materials III and IV are reacted with one another are generally from 0.9 to 1.2, preferably from 0.95 to 1.1, particularly preferably from 0.98 to 1.04, for the ratio of aroyl compound III to sulfamic acid amide IV.

The reaction is usually carried out at temperatures in the range from −30 to 100° C., preferably from −10 to 80° C., particularly preferably from 0 to 60° C.

The first reaction step is advantageously carried out under neutral conditions. If an acidic reaction product, for example hydrogen chloride (if X in formula III is halogen) is formed during the reaction, this is removed by addition of a basic compound. Suitable basic compounds include inorganic and organic bases. Suitable inorganic basic compounds are, for example, alkali metal or alkaline earth metal hydroxides, bicarbonates or carbonates. However, the reaction can also be carried out in the presence of an organic base, for example triethylamine, tri-n-propylamine, N-ethyldiisopropylamine, pyridine, α-, β-, γ-picoline, 2,4-, 2,6-lutidine, N-methylpyrrolidine, dimethylaniline, N,N-dimethylcyclohexylamine, quinoline or acridine. In general, an excess of base is employed, based on the compound III. The molar amount of base is from 1.0 to 2 mol, preferably from 1.02 to 1.3 mol, of base (calculated as base equivalent) per mole of the compound III. If appropriate, the reaction mixture contains pyridine or a pyridine compound, for example a 4-dialkylaminopyridine such as 4-dimethylaminopyridine, as catalyst. The added quantity of catalyst is about 0.1-10%, based on the compound III.

The reaction of the aroyl compounds III with the compounds of the formula IV is advantageously carried out in the presence of a solvent. Suitable solvents for these reactons are—depending on the temperature range—hydrocarbons, such as pentane, hexane, cyclopentane, cyclohexane, toluene, xylene, chlorinated hydrocarbons, such as methylene chloride, chloroform, 1,2-dichloroethane, 1,1,2,2-tetrachloroethane, chlorobenzene, 1,2-, 1,3- or 1,4-dichlorobenzene; ethers, such as 1,4-dioxane, anisole, glycol ethers, such as dimethyl glycol ether, diethyl glycol ether, diethylene glycol dimethyl ether; esters, such as ethyl acetate, propyl acetate, methyl isobutyrate, isobutyl acetate; carboxamides, such as N,N-dimethylformamide, N-methylpyrrolidone, nitrated hydrocarbons, such as nitrobenzene; tetraalkylureas, such as tetraethylurea, tetrabutylurea, dimethylethyleneurea, dimethylpropyleneurea; sulfoxides, such as dimethyl sulfoxide; sulfones, such as dimethyl sulfone, diethyl sulfone, tetramethylene sulfone; nitriles, such as acetonitrile, propionitrile, butyronitrile or isobutyronitrile; water; or else mixtures of individual solvents.

It is furthermore possible to carry out the reaction in an aqueous two-phase system, preferably in the presence of phase-transfer catalysts such as quaternary ammonium or phosphonium salts. Suitable reaction conditions for the two-phase reaction are those described in EP-A 556737.

Suitable for use as phase-transfer catalysts are quaternary ammonium or phosphonium salts. Suitable compounds which may be mentioned are the following: tetraalkyl-($C_1$-$C_{18}$)-ammonium chlorides, bromides or fluorides, N-benzyltrialkyl-($C_1$-$C_{18}$)-ammonium chlorides, bromides or fluorides, tetraalkyl-($C_1$-$C_{18}$)-phosphonium chlorides or bromides, tetraphenylphosphonium chloride or bromide, (phenyl)$_o$($C_1$-$C_{18}$-alkyl)$_p$-phosphonium chlorides or bromides, where o=1 to 3, p=3 to 1 and o+p=4. Particular preference is given to tetraethylammonium chloride and N-benzyltriethylammonium chloride. The amount of phase-transfer catalyst is generally up to 20% by weight, preferably from 1 to 15% by weight and particularly preferably from 2 to 8% by weight, based on the starting material IV.

The aroyl compound III is advantageously added over a period of from 0.25 to 2 hours to a mixture of the sulfamic acid amide IV and, if appropriate, the base in one of the above-mentioned solvents, and the mixture is stirred for another 0.5 to 16 hours, preferably 2 to 8 hours, until the reaction has gone to completion. The reaction temperature is generally from 0° C. to 60° C.

If an aqueous two-phase system is used, the starting materials III and IV can be added in any order with stirring to a mixture of the phase-transfer catalyst in the two phases, and the reaction can then be completed in the indicated temperature range by adding a base.

The reaction can be carried out continuously or batch-wise, at atmospheric pressure or under elevated pressure.

For work-up, the organic phase is extracted with dilute mineral acid such as hydrochloric acid, the organic phase is dried and the solvent is removed under reduced pressure. If appropriate, the residue can also be purified further by trituration with a solvent or solvent mixture, for example an aromatic hydrocarbon, such as benzene, xylene or toluene, or an aliphatic or cycloaliphatic hydrocarbon, such as petroleum ether, pentane, hexane or cyclohexane, an ether such as diethyl ether, etc., and mixtures of these, filtration with suction and drying.

The 2nd reaction step, i.e. the reduction of the nitro compound V to the compound II, is illustrated in more detail below.

The reduction of the compound V to the compound II can be effected, for example, using nascent hydrogen. To this end, the nitro compound is reacted with an acid in the presence of a base metal. According to their nature, base metals are dissolved by a Brönsted acid with evolution of hydrogen. Such metals generally have a normal potential of <0 V and in particular of ≦−0.1 V, for example in the range of from −0.1 to −1.0 V (in acidic aqueous solution at 15° C. and 1 bar). Examples of suitable metals are Zn, Fe and Sn, in particular Fe. Acids suitable for this purpose are both inorganic mineral acids, for example hydrochloric acid or dilute sulfuric acid, or mixtures of inorganic acid or one of the solvents mentioned above, for example gaseous HCl in an ether or an alcohol or a mixture thereof, and organic carboxylic acids, expediently acetic acid, propionic acid or butyric acid.

The reaction conditions correspond substantially to the reaction conditions used for reducing aliphatic or aromatic nitro groups to aliphatic or aromatic amino groups with nascent hydrogen (see, for example, H. Koopman, Rec. Tray. 80 (1961), 1075; see also N. Kornblum, L. Fischbein, J. Am. Chem. Soc. 77, (1955) 6266).

Depending on the type of metal and acid, the reaction temperature is generally in the range of from −20 to +120° C., with temperatures in the range of from 50 to 100° C. being preferred if alkanoic acids such as acetic acid are used. The reaction time can be from a few minutes to a number of hours, for example from about 20 minutes to 5 hours. Preferably, the compound V to be reduced is initially charged to the reaction vessel and the metal in question is then, preferably in finely divided form, in particular as a powder, added with mixing to the reaction mixture. The addition is preferably carried out over a period of from 10 minutes to 2 hours. It is, of course, also possible to initially charge the metal and the acid and to add the compound V, if appropriate together with an inert solvent. Frequently, the reaction mixture is allowed some extra reaction time at reaction temperature, for example from 10 minutes to 4 hours.

The reduction of V to II is preferably carried out using iron powder in dilute acid. Suitable acids are mineral acids, such as hydrochloric acid, or organic acids, such as formic acid, acetic acid, propionic acid, butyric acid. Preference is given to using acetic acid. The amount of iron powder is preferably from 2 to 5 mol, in particular from 2.5 to 4 mol, per mole of the compound V. The amount of acid is generally not critical. It is expedient to use an at least equimolar amount of acid, based on the nitro compound V, to reduce the starting material as completely as possible. The reaction can be carried out continuously or batch-wise. In this case, the reaction temperatures are in the range of from 50 to 100° C., preferably from 65 to 75° C. In one embodiment, for example, the iron powder is initially charged in acetic acid and the compound V is then added to the reaction vessel. The addition is preferably carried out over a period of from 20 to 60 minutes, with mixing of the components, for example by stirring. After the addition has ended, the mixture is allowed to react at reaction temperature for another 0.5 to 2 hours, preferably for about 1 hour. However, it is also possible to add the iron powder with stirring to the mixture of the compound V in glacial acetic acid and to bring the reaction to completion as described above.

Work-up for the isolation of the target product can be carried out by processes customary for this purpose. In general, the solvent is initially removed, for example by distillation. For further purification, it is possible to employ customary processes such as crystallization, chromatography, for example on silica gel, trituration with a solvent, for example an aromatic hydrocarbon, such as benzene, toluene or xylene, or an aliphatic hydrocarbon, such as petroleum ether, hexane, cyclohexane, pentane, a carboxylic ester, such as ethyl acetate, etc., and mixtures of these.

Suitable reducing agents are furthermore also metal hyrides and semimetal hydrides, such as aluminum hydride and hydrides derived therefrom, such as lithium aluminum hydride, diisobutylaluminum hydride; borohydrides, such as diborane and boranates derived therefrom, such as sodium borohydride or lithium borohydride. To this end, the nitro compound V is, in an inert solvent, brought into contact with the complex metal hydride at 10-65° C., advantageously at 20-50° C. The reaction time is preferably from 2 to 10 hours, advantageously from 3 to 6 hours. Reaction is preferably carried out in an organic solvent which is inert to the reducing agent. Suitable solvents are—depending on the chosen reducing agent—for example alcohols, e.g. $C_1$-$C_4$-alcohols, such as methanol, ethanol, n-propanol, isopropanol or n-butanol, and their mixtures with water, or ethers, such as diisopropyl ether, methyl tert-butyl ether, ethylene glycol dimethyl ether, dioxane or tetrahydrofuran.

In general, from 0.5 to 3, advantageously from 0.75 to 2.5, mol of metal hydride, semimetal hydride, borohydride or boranate are employed per mole of nitro compound V. The process follows the procedure described in Organikum, VEB Deutscher Verlag der Wissenschaften, Berlin 1976, 15th edition, pp. 612-616.

A further reducing agent suitable for converting the compound V into the compound II is hydrogen in the presence of catalytic amounts of transition metals or transition metal compounds, in particular those of the 8th transition group. Preferred transition metals are, for example, nickel, palladium, platinum, ruthenium or rhodium. The transition metals can be employed as such or in supported form. Examples of supports are activated carbon, alumina, $ZrO_2$, $TiO_2$, $SiO_2$, carbonates and the like. The transition metals can also be employed in the form of activated metals such as Raney nickel. The transition metals can also be used in the form of compounds. Suitable transition metal compounds are, for example, palladium oxide and platinum oxide. The catalysts are generally employed in an amount of from 0.05 to 10.0 mol % (calculated as metal), based on the compound V to be reduced. The reaction is carried out either in the absence of a solvent or in an inert solvent or diluent. Solvents or diluents suitable for the reaction are, depending on the solubility of the substrate to be hydrated and the chosen reducing agent, for example carboxylic acids, such as acetic acid, or aqueous solutions of organic acids, such as acetic acid and water, carboxylic acid esters, such as ethyl acetate, $C_1$-$C_4$-alcohols, such as methanol, ethanol, n-propanol, isopropanol, n-butanol or aromatic hydrocarbons, such as toluene. Following removal of the catalyst, the reaction solution can be worked up in a customary manner to afford the product. The hydration can be carried out at atmospheric pressure or under an elevated hydrogen pressure, for example at a hydrogen pressure of from 0.01 to 50 bar, preferably from 0.1 to 40 bar. For the catalytic hydration of aromatic nitro compounds, see, for example, Rylander in "Catalytic Hydrogenation over Platinum Metals", Academic Press, New York, 1967, 168-202; Furst et al., Chem. Rev. 65 (1965), 52; Tepko et al., J. Org. Chem. 45, (1980), 4992.

In the case of chlorine-containing benzoylsulfamides, the hydration is, depending on the sensitivity of the substituents, carried out at from 20 to 170° C., expediently at from 20 to 140° C., advantageously at from 20 to 80° C. In the case of reactive halogen substituents, it is furthermore recommended to carry out the hydration in neutral solution, preferably at only slightly elevated pressure, using small amounts of nickel, platinum or else rhodium catalysts; also suitable are noble metal sulfides, such as platinum sulfide. The process is described in detail in Houben-Weyl, "Methoden der organischen Chemie", Vol. IV/1C, pp. 520-526.

The reduction of the compound V to the compound II can also be carried out using sodium sulfide, advantageously in aqueous ammonia solution, in the presence of ammonium chloride, in accordance with the process described in Org. Syn., Coll. Vol., 3 (1955), 82. The reaction temperature is generally from 40 to 90° C., preferably from 60 to 80° C. Expediently, from 3 to 4 mol of sodium sulfide are employed per mol of nitro compound V.

The aroyl compounds III used in Scheme 2 can be obtained by processes known in the prior art or be prepared similarly to known processes, for example in accordance with U.S. Pat. No. 6,251,829, EP 415 641, EP 908 457, EP 1176133 and WO 01/087872.

The sulfamic acid amides IV are known in the prior art or can be prepared by known processes, for example in accordance with the German patent application DE 102 21 910.0 by reaction of ammonia with sulfamic acid halides. The disclosure of this publication is hereby incorporated by way of reference.

The sulfamic acid amides IV are preferably prepared by the process described in the not yet published German patent application DE 102 21 910.0. This process comprises the following steps: (i) reaction of a primary or secondary amine with an at least equimolar amount of $SO_3$ or an $SO_3$ source in the presence of at least equimolar amounts of a tertiary amine, based in each case on the primary or secondary amine, giving an amidosulfonic acid ammonium salt; (ii) reaction of the amidosulfonic acid ammonium salt with an at least stoichiometric amount of a phosphorus halide, giving a sulfamic acid halide, and (iii) reaction of the sulfamic acid halide obtained in step ii) with ammonia, giving the sulfamic acid amide V.

The process according to the invention allows, for the first time, the preparation of iso(thio)cyanatobenzoylsulfamic acid amides of the formula I. The compounds I are novel and also form part of the subject-matter of the present invention.

Among the iso(thio)cyanatobenzoylsulfamic acid amides of the formula I, preference is given to those of the formula IA, where the variables $R^a$, $R^b$, $R^c$, $R^d$ are as defined above.

Very particular preference is given to the compounds of the formula IA.1,

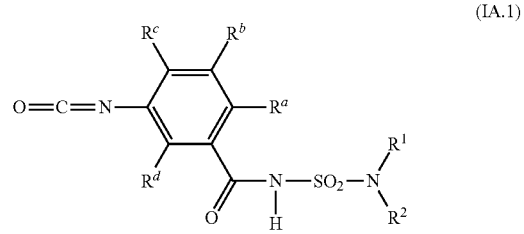

(IA.1)

where the variables $R^1$, $R^2$, $R^a$, $R^b$, $R^c$, $R^d$ are as defined above.

Among the iso(thio)cyanatobenzoylsulfamic acid amides of the formula IA.1, particular preference is given to those in which the variables $R^1$, $R^2$, $R^a$, $R^b$, $R^c$, $R^d$ independently of one another, but preferably in combination, are as defined below:

$R^a$ is cyano or halogen, in particular cyano, fluorine or chlorine;
$R^b$ is hydrogen;
$R^c$ is hydrogen or halogen, in particular hydrogen, fluorine or chlorine;
$R^d$ is hydrogen;
$R^1$ and $R^2$ independently of one another are hydrogen, $C_1$-$C_6$-alkyl which is optionally substituted by a substituent selected from the group consisting of halogen, cyano, $C_1$-$C_4$-alkoxy, $C_1$-$C_4$-alkoxycarbonyl, $C_1$-$C_4$-alkylthio, $C_3$-$C_8$-cycloalkyl, furyl, thienyl, 1,3-dioxolanyl, phenyl which for its part is optionally substituted by halogen or $C_1$-$C_4$-alkoxy, $C_2$-$C_6$-alkenyl, $C_2$-$C_6$-alkynyl, $C_3$-$C_8$-cycloalkyl or phenyl which is optionally substituted by 1 or 2 substituents selected from the group consisting of halogen, $C_1$-$C_4$-alkyl, $C_1$-$C_4$-fluoroalkyl, $C_1$-$C_4$-alkoxy, $C_1$-$C_4$-alkoxycarbonyl, nitro and $C_1$-$C_3$-dialkylamino, naphthyl or pyridyl or $R^1$ and $R^2$ together form a five-, six- or seven-membered saturated or unsaturated nitrogen heterocycle which may optionally contain a further heteroatom selected from the group consisting of N, a group $NR^6$ (where $R^6$ is as defined above) and O as ring member and/or which may be substituted by one, two or three substituents selected from the group consisting of $C_1$-$C_4$-alkyl and $C_1$-$C_4$-halogenalkyl.

In particular, one of the radicals $R^1$ or $R^2$ is hydrogen, $C_1$-$C_8$-alkyl, $C_2$-$C_6$-alkenyl or $C_2$-$C_6$-alkynyl and the other radical $R^1$ or $R^2$ is $C_1$-$C_8$-alkyl, $C_3$-$C_8$-cycloalkyl or phenyl.

Very particular preference is given to the isocyanatobenzoylsulfamic acid amides of the formula IA.1-a (≡I where W=oxygen, Ar=Ar-1 where $R^a$=Cl and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds IA.1-a.1 to IA.1-a.495 in which the variables $R^1$, $R^2$ together have the meanings given in one row of Table 1.

TABLE 1

(IA.1-a)

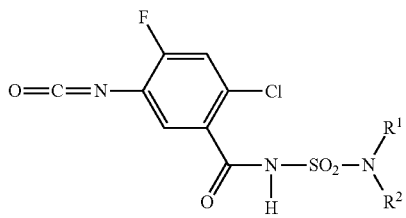

| No. | $R^1$ | $R^2$ |
|---|---|---|
| 1 | H | $CH_3$ |
| 2 | H | $C_2H_5$ |
| 3 | H | $CH_2CH_2$—Cl |
| 4 | H | $CH_2CH_2$—CN |
| 5 | H | $CH_2$—CO—$OCH_3$ |
| 6 | H | $CH_2$—CO—$OC_2H_5$ |
| 7 | H | $CH(CH_3)$—CO—$OCH_3$ |
| 8 | H | $CH_2CH_2$—$OCH_3$ |
| 9 | H | $CH_2$—$C_2H_5$ |
| 10 | H | $CH_2CH_2$—$C_2H_5$ |
| 11 | H | $CH(CH_3)_2$ |
| 12 | H | $CH(CH_3)$—$C_2H_5$ |
| 13 | H | $CH_2$—$CH(CH_3)_2$ |
| 14 | H | $C(CH_3)_3$ |
| 15 | H | $CH(CH_3)$—$CH_2$—$C_2H_5$ |
| 16 | H | $CH_2$—$CH(CH_3)$—$C_2H_5$ |
| 17 | H | $CH_2CH_2$—$CH(CH_3)_2$ |
| 18 | H | $CH_2$—CH=$CH_2$ |
| 19 | H | $CH(CH_3)$=$CH_2$ |
| 20 | H | $CH_2$=CH—$CH_3$ |
| 21 | H | $CH_2$—C≡CH |
| 22 | H | $CH(CH_3)$—C≡CH |
| 23 | H | cyclopropyl |
| 24 | H | $CH_2$-cyclopropyl |
| 25 | H | cyclopentyl |
| 26 | H | $CH_2$-cyclopentyl |
| 27 | H | $CH_2$-(1,3-dioxolan-2-yl) |

TABLE 1-continued (IA.1-a)

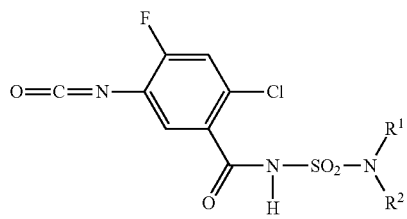

| No. | $R^1$ | $R^2$ |
|---|---|---|
| 28 | H | $CH_2$-(2-furyl) |
| 29 | H | $CH_2$-(3-furyl) |
| 30 | H | $CH_2$-(2-thienyl) |
| 31 | H | $CH_2$-(3-thienyl) |
| 32 | H | phenyl |
| 33 | H | 2-chlorophenyl |
| 34 | H | 3-chlorophenyl |
| 35 | H | 4-chlorophenyl |
| 36 | H | 2-fluorophenyl |
| 37 | H | 3-fluorophenyl |
| 38 | H | 4-fluorophenyl |
| 39 | H | 2-methylphenyl |
| 40 | H | 3-methylphenyl |
| 41 | H | 4-methylphenyl |
| 42 | H | 2-methoxyphenyl |
| 43 | H | 3-methoxyphenyl |
| 44 | H | 4-methoxyphenyl |
| 45 | H | 2-(methoxycarbonyl)phenyl |
| 46 | H | 3-(methoxycarbonyl)phenyl |
| 47 | H | 4-(methoxycarbonyl)phenyl |
| 48 | H | 2-nitrophenyl |
| 49 | H | 3-nitrophenyl |
| 50 | H | 4-nitrophenyl |
| 51 | H | 2-(dimethylamino)phenyl |
| 52 | H | 3-(dimethylamino)phenyl |
| 53 | H | 4-(dimethylamino)phenyl |
| 54 | H | 2-(trifluoromethyl)phenyl |
| 55 | H | 3-(trifluoromethyl)phenyl |
| 56 | H | 4-(trifluoromethyl)phenyl |
| 57 | H | 3-(phenoxy)phenyl |
| 58 | H | 4-(phenoxy)phenyl |
| 59 | H | 2,4-difluorophenyl |
| 60 | H | 2,4-dichlorophenyl |
| 61 | H | 3,4-difluorophenyl |
| 62 | H | 3,4-dichlorophenyl |
| 63 | H | 3,5-difluorophenyl |
| 64 | H | 3,5-dichlorophenyl |
| 65 | H | 2-pyridyl |
| 66 | H | 3-pyridyl |
| 67 | H | 4-pyridyl |
| 68 | H | α-naphthyl |
| 69 | H | benzyl |
| 70 | H | 2-chlorobenzyl |
| 71 | H | 3-chlorobenzyl |
| 72 | H | 4-chlorobenzyl |
| 73 | H | 2-methoxybenzyl |
| 74 | H | 3-methoxybenzyl |
| 75 | H | 4-methoxybenzyl |
| 76 | $CH_3$ | $CH_3$ |
| 77 | $CH_3$ | $C_2H_5$ |
| 78 | $CH_3$ | $CH_2CH_2$—Cl |
| 79 | $CH_3$ | $CH_2CH_2$—CN |
| 80 | $CH_3$ | $CH_2$—CO—$OCH_3$ |
| 81 | $CH_3$ | $CH_2$—CO—$OC_2H_5$ |
| 82 | $CH_3$ | $CH(CH_3)$—CO—$OCH_3$ |
| 83 | $CH_3$ | $CH_2CH_2$—$OCH_3$ |
| 84 | $CH_3$ | $CH_2$—$C_2H_5$ |
| 85 | $CH_3$ | $CH_2CH_2$—$C_2H_5$ |
| 86 | $CH_3$ | $CH(CH_3)_2$ |
| 87 | $CH_3$ | $CH(CH_3)$—$C_2H_5$ |
| 88 | $CH_3$ | $CH_2$—$CH(CH_3)_2$ |
| 89 | $CH_3$ | $C(CH_3)_3$ |
| 90 | $CH_3$ | $CH(CH_3)$—$CH_2$—$C_2H_5$ |
| 91 | $CH_3$ | $CH_2$—$CH(CH_3)$—$C_2H_5$ |
| 92 | $CH_3$ | $CH_2CH_2$—$CH(CH_3)_2$ |

TABLE 1-continued

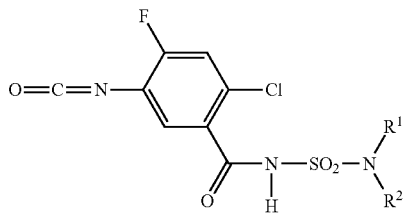

(IA.1-a)

| No. | R¹ | R² |
|---|---|---|
| 93 | CH₃ | CH₂—CH=CH₂ |
| 94 | CH₃ | CH(CH₃)=CH₂ |
| 95 | CH₃ | CH₂=CH—CH₃ |
| 96 | CH₃ | CH₂—C≡CH |
| 97 | CH₃ | CH(CH₃)—C≡CH |
| 98 | CH₃ | cyclopropyl |
| 99 | CH₃ | CH₂-cyclopropyl |
| 100 | CH₃ | cyclopentyl |
| 101 | CH₃ | CH₂-cyclopentyl |
| 102 | CH₃ | CH₂-(1,3-dioxolan-2-yl) |
| 103 | CH₃ | CH₂-(2-furyl) |
| 104 | CH₃ | CH₂-(3-furyl) |
| 105 | CH₃ | CH₂-(2-thienyl) |
| 106 | CH₃ | CH₂-(3-thienyl) |
| 107 | CH₃ | phenyl |
| 108 | CH₃ | 2-chlorophenyl |
| 109 | CH₃ | 3-chlorophenyl |
| 110 | CH₃ | 4-chlorophenyl |
| 111 | CH₃ | 2-fluorophenyl |
| 112 | CH₃ | 3-fluorophenyl |
| 113 | CH₃ | 4-fluorophenyl |
| 114 | CH₃ | 2-methylphenyl |
| 115 | CH₃ | 3-methylphenyl |
| 116 | CH₃ | 4-methylphenyl |
| 117 | CH₃ | 2-methoxyphenyl |
| 118 | CH₃ | 3-methoxyphenyl |
| 119 | CH₃ | 4-methoxyphenyl |
| 120 | CH₃ | 2-(methoxycarbonyl)phenyl |
| 121 | CH₃ | 3-(methoxycarbonyl)phenyl |
| 122 | CH₃ | 4-(methoxycarbonyl)phenyl |
| 123 | CH₃ | 2-nitrophenyl |
| 124 | CH₃ | 3-nitrophenyl |
| 125 | CH₃ | 4-nitrophenyl |
| 126 | CH₃ | 2-(dimethylamino)phenyl |
| 127 | CH₃ | 3-(dimethylamino)phenyl |
| 128 | CH₃ | 4-(dimethylamino)phenyl |
| 129 | CH₃ | 2-(trifluoromethyl)phenyl |
| 130 | CH₃ | 3-(trifluoromethyl)phenyl |
| 131 | CH₃ | 4-(trifluoromethyl)phenyl |
| 132 | CH₃ | 3-(phenoxy)phenyl |
| 133 | CH₃ | 4-(phenoxy)phenyl |
| 134 | CH₃ | 2,4-difluorophenyl |
| 135 | CH₃ | 2,4-dichlorophenyl |
| 136 | CH₃ | 3,4-difluorophenyl |
| 137 | CH₃ | 3,4-dichlorophenyl |
| 138 | CH₃ | 3,5-difluorophenyl |
| 139 | CH₃ | 3,5-dichlorophenyl |
| 140 | CH₃ | 2-pyridyl |
| 141 | CH₃ | 3-pyridyl |
| 142 | CH₃ | 4-pyridyl |
| 143 | CH₃ | α-naphthyl |
| 144 | CH₃ | benzyl |
| 145 | CH₃ | 2-chlorobenzyl |
| 146 | CH₃ | 3-chlorobenzyl |
| 147 | CH₃ | 4-chlorobenzyl |
| 148 | CH₃ | 2-methoxybenzyl |
| 149 | CH₃ | 3-methoxybenzyl |
| 150 | CH₃ | 4-methoxybenzyl |
| 151 | C₂H₅ | C₂H₅ |
| 152 | C₂H₅ | CH₂CH₂—Cl |
| 153 | C₂H₅ | CH₂CH₂—CN |
| 154 | C₂H₅ | CH₂—CO—OCH₃ |
| 155 | C₂H₅ | CH₂—CO—OC₂H₅ |
| 156 | C₂H₅ | CH(CH₃)—CO—OCH₃ |
| 157 | C₂H₅ | CH₂CH₂—OCH₃ |
| 158 | C₂H₅ | CH₂—C₂H₅ |
| 159 | C₂H₅ | CH₂CH₂—C₂H₅ |
| 160 | C₂H₅ | CH(CH₃)₂ |
| 161 | C₂H₅ | CH(CH₃)—C₂H₅ |
| 162 | C₂H₅ | CH₂—CH(CH₃)₂ |
| 163 | C₂H₅ | C(CH₃)₃ |
| 164 | C₂H₅ | CH(CH₃)—CH₂—C₂H₅ |
| 165 | C₂H₅ | CH₂—CH(CH₃)—C₂H₅ |
| 166 | C₂H₅ | CH₂CH₂—CH(CH₃)₂ |
| 167 | C₂H₅ | CH₂—CH=CH₂ |
| 168 | C₂H₅ | CH(CH₃)=CH₂ |
| 169 | C₂H₅ | CH₂=CH—CH₃ |
| 170 | C₂H₅ | CH₂—C≡CH |
| 171 | C₂H₅ | CH(CH₃)—C≡CH |
| 172 | C₂H₅ | cyclopropyl |
| 173 | C₂H₅ | CH₂-cyclopropyl |
| 174 | C₂H₅ | cyclopentyl |
| 175 | C₂H₅ | CH₂-cyclopentyl |
| 176 | C₂H₅ | CH₂-(1,3-dioxolan-2-yl) |
| 177 | C₂H₅ | CH₂-(2-furyl) |
| 178 | C₂H₅ | CH₂-(3-furyl) |
| 179 | C₂H₅ | CH₂-(2-thienyl) |
| 180 | C₂H₅ | CH₂-(3-thienyl) |
| 181 | C₂H₅ | phenyl |
| 182 | C₂H₅ | 2-chlorophenyl |
| 183 | C₂H₅ | 3-chlorophenyl |
| 184 | C₂H₅ | 4-chlorophenyl |
| 185 | C₂H₅ | 2-fluorophenyl |
| 186 | C₂H₅ | 3-fluorophenyl |
| 187 | C₂H₅ | 4-fluorophenyl |
| 188 | C₂H₅ | 2-methylphenyl |
| 189 | C₂H₅ | 3-methylphenyl |
| 190 | C₂H₅ | 4-methylphenyl |
| 191 | C₂H₅ | 2-methoxyphenyl |
| 192 | C₂H₅ | 3-methoxyphenyl |
| 193 | C₂H₅ | 4-methoxyphenyl |
| 194 | C₂H₅ | 2-(methoxycarbonyl)phenyl |
| 195 | C₂H₅ | 3-(methoxycarbonyl)phenyl |
| 196 | C₂H₅ | 4-(methoxycarbonyl)phenyl |
| 197 | C₂H₅ | 2-nitrophenyl |
| 198 | C₂H₅ | 3-nitrophenyl |
| 199 | C₂H₅ | 4-nitrophenyl |
| 200 | C₂H₅ | 2-(dimethylamino)phenyl |
| 201 | C₂H₅ | 3-(dimethylamino)phenyl |
| 202 | C₂H₅ | 4-(dimethylamino)phenyl |
| 203 | C₂H₅ | 2-(trifluoromethyl)phenyl |
| 204 | C₂H₅ | 3-(trifluoromethyl)phenyl |
| 205 | C₂H₅ | 4-(trifluoromethyl)phenyl |
| 206 | C₂H₅ | 3-(phenoxy)phenyl |
| 207 | C₂H₅ | 4-(phenoxy)phenyl |
| 208 | C₂H₅ | 2,4-difluorophenyl |
| 209 | C₂H₅ | 2,4-dichlorophenyl |
| 210 | C₂H₅ | 3,4-difluorophenyl |
| 211 | C₂H₅ | 3,4-dichlorophenyl |
| 212 | C₂H₅ | 3,5-difluorophenyl |
| 213 | C₂H₅ | 3,5-dichlorophenyl |
| 214 | C₂H₅ | 2-pyridyl |
| 215 | C₂H₅ | 3-pyridyl |
| 216 | C₂H₅ | 4-pyridyl |
| 217 | C₂H₅ | α-naphthyl |
| 218 | C₂H₅ | benzyl |
| 219 | C₂H₅ | 2-chlorobenzyl |
| 220 | C₂H₅ | 3-chlorobenzyl |
| 221 | C₂H₅ | 4-chlorobenzyl |
| 222 | C₂H₅ | 2-methoxybenzyl |

TABLE 1-continued (IA.1-a)

| No. | R¹ | R² |
|---|---|---|
| 223 | C$_2$H$_5$ | 3-methoxybenzyl |
| 224 | C$_2$H$_5$ | 4-methoxybenzyl |
| 225 | CH$_2$—C$_2$H$_5$ | C$_2$H$_5$ |
| 226 | CH$_2$—C$_2$H$_5$ | CH$_2$CH$_2$—Cl |
| 227 | CH$_2$—C$_2$H$_5$ | CH$_2$CH$_2$—CN |
| 228 | CH$_2$—C$_2$H$_5$ | CH$_2$—CO—OCH$_3$ |
| 229 | CH$_2$—C$_2$H$_5$ | CH$_2$—CO—OC$_2$H$_5$ |
| 230 | CH$_2$—C$_2$H$_5$ | CH(CH$_3$)—CO—OCH$_3$ |
| 231 | CH$_2$—C$_2$H$_5$ | CH$_2$CH$_2$—OCH$_3$ |
| 232 | CH$_2$—C$_2$H$_5$ | CH$_2$—C$_2$H$_5$ |
| 233 | CH$_2$—C$_2$H$_5$ | CH$_2$CH$_2$—C$_2$H$_5$ |
| 234 | CH$_2$—C$_2$H$_5$ | CH(CH$_3$)$_2$ |
| 235 | CH$_2$—C$_2$H$_5$ | CH(CH$_3$)—C$_2$H$_5$ |
| 236 | CH$_2$—C$_2$H$_5$ | CH$_2$—CH(CH$_3$)$_2$ |
| 237 | CH$_2$—C$_2$H$_5$ | C(CH$_3$)$_3$ |
| 238 | CH$_2$—C$_2$H$_5$ | CH(CH$_3$)—CH$_2$—C$_2$H$_5$ |
| 239 | CH$_2$—C$_2$H$_5$ | CH$_2$—CH(CH$_3$)—C$_2$H$_5$ |
| 240 | CH$_2$—C$_2$H$_5$ | CH$_2$CH$_2$—CH(CH$_3$)$_2$ |
| 241 | CH$_2$—C$_2$H$_5$ | CH$_2$—CH═CH$_2$ |
| 242 | CH$_2$—C$_2$H$_5$ | CH(CH$_3$)═CH$_2$ |
| 243 | CH$_2$—C$_2$H$_5$ | CH$_2$═CH—CH$_3$ |
| 244 | CH$_2$—C$_2$H$_5$ | CH$_2$—C≡CH |
| 245 | CH$_2$—C$_2$H$_5$ | CH(CH$_3$)—C≡CH |
| 246 | CH$_2$—C$_2$H$_5$ | cyclopropyl |
| 247 | CH$_2$—C$_2$H$_5$ | CH$_2$-cyclopropyl |
| 248 | CH$_2$—C$_2$H$_5$ | cyclopentyl |
| 249 | CH$_2$—C$_2$H$_5$ | CH$_2$-cyclopentyl |
| 250 | CH$_2$—C$_2$H$_5$ | CH$_2$-(1,3-dioxolan-2-yl) |
| 251 | CH$_2$—C$_2$H$_5$ | CH$_2$-(2-furyl) |
| 252 | CH$_2$—C$_2$H$_5$ | CH$_2$-(3-furyl) |
| 253 | CH$_2$—C$_2$H$_5$ | CH$_2$-(2-thienyl) |
| 254 | CH$_2$—C$_2$H$_5$ | CH$_2$-(3-thienyl) |
| 255 | CH$_2$—C$_2$H$_5$ | phenyl |
| 256 | CH$_2$—C$_2$H$_5$ | 2-chlorophenyl |
| 257 | CH$_2$—C$_2$H$_5$ | 3-chlorophenyl |
| 258 | CH$_2$—C$_2$H$_5$ | 4-chlorophenyl |
| 259 | CH$_2$—C$_2$H$_5$ | 2-fluorophenyl |
| 260 | CH$_2$—C$_2$H$_5$ | 3-fluorophenyl |
| 261 | CH$_2$—C$_2$H$_5$ | 4-fluorophenyl |
| 262 | CH$_2$—C$_2$H$_5$ | 2-methylphenyl |
| 263 | CH$_2$—C$_2$H$_5$ | 3-methylphenyl |
| 264 | CH$_2$—C$_2$H$_5$ | 4-methylphenyl |
| 265 | CH$_2$—C$_2$H$_5$ | 2-methoxyphenyl |
| 266 | CH$_2$—C$_2$H$_5$ | 3-methoxyphenyl |
| 267 | CH$_2$—C$_2$H$_5$ | 4-methoxyphenyl |
| 268 | CH$_2$—C$_2$H$_5$ | 2-(methoxycarbonyl)phenyl |
| 269 | CH$_2$—C$_2$H$_5$ | 3-(methoxycarbonyl)phenyl |
| 270 | CH$_2$—C$_2$H$_5$ | 4-(methoxycarbonyl)phenyl |
| 271 | CH$_2$—C$_2$H$_5$ | 2-nitrophenyl |
| 272 | CH$_2$—C$_2$H$_5$ | 3-nitrophenyl |
| 273 | CH$_2$—C$_2$H$_5$ | 4-nitrophenyl |
| 274 | CH$_2$—C$_2$H$_5$ | 2-(dimethylamino)phenyl |
| 275 | CH$_2$—C$_2$H$_5$ | 3-(dimethylamino)phenyl |
| 276 | CH$_2$—C$_2$H$_5$ | 4-(dimethylamino)phenyl |
| 277 | CH$_2$—C$_2$H$_5$ | 2-(trifluoromethyl)phenyl |
| 278 | CH$_2$—C$_2$H$_5$ | 3-(trifluoromethyl)phenyl |
| 279 | CH$_2$—C$_2$H$_5$ | 4-(trifluoromethyl)phenyl |
| 280 | CH$_2$—C$_2$H$_5$ | 3-(phenoxy)phenyl |
| 281 | CH$_2$—C$_2$H$_5$ | 4-(phenoxy)phenyl |
| 282 | CH$_2$—C$_2$H$_5$ | 2,4-difluorophenyl |
| 283 | CH$_2$—C$_2$H$_5$ | 2,4-dichlorophenyl |
| 284 | CH$_2$—C$_2$H$_5$ | 3,4-difluorophenyl |
| 285 | CH$_2$—C$_2$H$_5$ | 3,4-dichlorophenyl |
| 286 | CH$_2$—C$_2$H$_5$ | 3,5-difluorophenyl |
| 287 | CH$_2$—C$_2$H$_5$ | 3,5-dichlorophenyl |
| 288 | CH$_2$—C$_2$H$_5$ | 2-pyridyl |
| 289 | CH$_2$—C$_2$H$_5$ | 3-pyridyl |
| 290 | CH$_2$—C$_2$H$_5$ | 4-pyridyl |
| 291 | CH$_2$—C$_2$H$_5$ | α-naphthyl |
| 292 | CH$_2$—C$_2$H$_5$ | benzyl |
| 293 | CH$_2$—C$_2$H$_5$ | 2-chlorobenzyl |
| 294 | CH$_2$—C$_2$H$_5$ | 3-chlorobenzyl |
| 295 | CH$_2$—C$_2$H$_5$ | 4-chlorobenzyl |
| 296 | CH$_2$—C$_2$H$_5$ | 2-methoxybenzyl |
| 297 | CH$_2$—C$_2$H$_5$ | 3-methoxybenzyl |
| 298 | CH$_2$—C$_2$H$_5$ | 4-methoxybenzyl |
| 299 | CH$_2$—CH$_2$—C$_2$H$_5$ | CH$_2$CH$_2$—Cl |
| 300 | CH$_2$—CH$_2$—C$_2$H$_5$ | CH$_2$CH$_2$—CN |
| 301 | CH$_2$—CH$_2$—C$_2$H$_5$ | CH$_2$—CO—OCH$_3$ |
| 302 | CH$_2$—CH$_2$—C$_2$H$_5$ | CH$_2$—CO—OC$_2$H$_5$ |
| 303 | CH$_2$—CH$_2$—C$_2$H$_5$ | CH(CH$_3$)—CO—OCH$_3$ |
| 304 | CH$_2$—CH$_2$—C$_2$H$_5$ | CH$_2$CH$_2$—OCH$_3$ |
| 305 | CH$_2$—CH$_2$—C$_2$H$_5$ | CH$_2$CH$_2$—C$_2$H$_5$ |
| 306 | CH$_2$—CH$_2$—C$_2$H$_5$ | CH(CH$_3$)$_2$ |
| 307 | CH$_2$—CH$_2$—C$_2$H$_5$ | CH(CH$_3$)—C$_2$H$_5$ |
| 308 | CH$_2$—CH$_2$—C$_2$H$_5$ | CH$_2$—CH(CH$_3$)$_2$ |
| 309 | CH$_2$—CH$_2$—C$_2$H$_5$ | C(CH$_3$)$_3$ |
| 310 | CH$_2$—CH$_2$—C$_2$H$_5$ | CH(CH$_3$)—CH$_2$—C$_2$H$_5$ |
| 311 | CH$_2$—CH$_2$—C$_2$H$_5$ | CH$_2$—CH(CH$_3$)—C$_2$H$_5$ |
| 312 | CH$_2$—CH$_2$—C$_2$H$_5$ | CH$_2$CH$_2$—CH(CH$_3$)$_2$ |
| 313 | CH$_2$—CH$_2$—C$_2$H$_5$ | CH$_2$—CH═CH$_2$ |
| 314 | CH$_2$—CH$_2$—C$_2$H$_5$ | CH(CH$_3$)═CH$_2$ |
| 315 | CH$_2$—CH$_2$—C$_2$H$_5$ | CH$_2$═CH—CH$_3$ |
| 316 | CH$_2$—CH$_2$—C$_2$H$_5$ | CH$_2$—C≡CH |
| 317 | CH$_2$—CH$_2$—C$_2$H$_5$ | CH(CH$_3$)—C≡CH |
| 318 | CH$_2$—CH$_2$—C$_2$H$_5$ | cyclopropyl |
| 319 | CH$_2$—CH$_2$—C$_2$H$_5$ | CH$_2$-cyclopropyl |
| 320 | CH$_2$—CH$_2$—C$_2$H$_5$ | cyclopentyl |
| 321 | CH$_2$—CH$_2$—C$_2$H$_5$ | CH$_2$-cyclopentyl |
| 322 | CH$_2$—CH$_2$—C$_2$H$_5$ | CH$_2$-(1,3-dioxolan-2-yl) |
| 323 | CH$_2$—CH$_2$—C$_2$H$_5$ | CH$_2$-(2-furyl) |
| 324 | CH$_2$—CH$_2$—C$_2$H$_5$ | CH$_2$-(3-furyl) |
| 325 | CH$_2$—CH$_2$—C$_2$H$_5$ | CH$_2$-(2-thienyl) |
| 326 | CH$_2$—CH$_2$—C$_2$H$_5$ | CH$_2$-(3-thienyl) |
| 327 | CH$_2$—CH$_2$—C$_2$H$_5$ | phenyl |
| 328 | CH$_2$—CH$_2$—C$_2$H$_5$ | 2-chlorophenyl |
| 329 | CH$_2$—CH$_2$—C$_2$H$_5$ | 3-chlorophenyl |
| 330 | CH$_2$—CH$_2$—C$_2$H$_5$ | 4-chlorophenyl |
| 331 | CH$_2$—CH$_2$—C$_2$H$_5$ | 2-fluorophenyl |
| 332 | CH$_2$—CH$_2$—C$_2$H$_5$ | 3-fluorophenyl |
| 333 | CH$_2$—CH$_2$—C$_2$H$_5$ | 4-fluorophenyl |
| 334 | CH$_2$—CH$_2$—C$_2$H$_5$ | 2-methylphenyl |
| 335 | CH$_2$—CH$_2$—C$_2$H$_5$ | 3-methylphenyl |
| 336 | CH$_2$—CH$_2$—C$_2$H$_5$ | 4-methylphenyl |
| 337 | CH$_2$—CH$_2$—C$_2$H$_5$ | 2-methoxyphenyl |
| 338 | CH$_2$—CH$_2$—C$_2$H$_5$ | 3-methoxyphenyl |
| 339 | CH$_2$—CH$_2$—C$_2$H$_5$ | 4-methoxyphenyl |
| 340 | CH$_2$—CH$_2$—C$_2$H$_5$ | 2-(methoxycarbonyl)phenyl |
| 341 | CH$_2$—CH$_2$—C$_2$H$_5$ | 3-(methoxycarbonyl)phenyl |
| 342 | CH$_2$—CH$_2$—C$_2$H$_5$ | 4-(methoxycarbonyl)phenyl |
| 343 | CH$_2$—CH$_2$—C$_2$H$_5$ | 2-nitrophenyl |
| 344 | CH$_2$—CH$_2$—C$_2$H$_5$ | 3-nitrophenyl |
| 345 | CH$_2$—CH$_2$—C$_2$H$_5$ | 4-nitrophenyl |
| 346 | CH$_2$—CH$_2$—C$_2$H$_5$ | 2-(dimethylamino)phenyl |
| 347 | CH$_2$—CH$_2$—C$_2$H$_5$ | 3-(dimethylamino)phenyl |
| 348 | CH$_2$—CH$_2$—C$_2$H$_5$ | 4-(dimethylamino)phenyl |
| 349 | CH$_2$—CH$_2$—C$_2$H$_5$ | 2-(trifluoromethyl)phenyl |
| 350 | CH$_2$—CH$_2$—C$_2$H$_5$ | 3-(trifluoromethyl)phenyl |
| 351 | CH$_2$—CH$_2$—C$_2$H$_5$ | 4-(trifluoromethyl)phenyl |
| 352 | CH$_2$—CH$_2$—C$_2$H$_5$ | 3-(phenoxy)phenyl |

TABLE 1-continued (IA.1-a)

structure: 4-fluoro-5-isocyanato-2-chloro-benzoyl-NH-SO2-N(R1)(R2)

| No. | R¹ | R² |
|---|---|---|
| 353 | CH₂—CH₂—C₂H₅ | 4-(phenoxy)phenyl |
| 354 | CH₂—CH₂—C₂H₅ | 2,4-difluorophenyl |
| 355 | CH₂—CH₂—C₂H₅ | 2,4-dichlorophenyl |
| 356 | CH₂—CH₂—C₂H₅ | 3,4-difluorophenyl |
| 357 | CH₂—CH₂—C₂H₅ | 3,4-dichlorophenyl |
| 358 | CH₂—CH₂—C₂H₅ | 3,5-difluorophenyl |
| 359 | CH₂—CH₂—C₂H₅ | 3,5-dichlorophenyl |
| 360 | CH₂—CH₂—C₂H₅ | 2-pyridyl |
| 361 | CH₂—CH₂—C₂H₅ | 3-pyridyl |
| 362 | CH₂—CH₂—C₂H₅ | 4-pyridyl |
| 363 | CH₂—CH₂—C₂H₅ | α-naphthyl |
| 364 | CH₂—CH₂—C₂H₅ | benzyl |
| 365 | CH₂—CH₂—C₂H₅ | 2-chlorobenzyl |
| 366 | CH₂—CH₂—C₂H₅ | 3-chlorobenzyl |
| 367 | CH₂—CH₂—C₂H₅ | 4-chlorobenzyl |
| 368 | CH₂—CH₂—C₂H₅ | 2-methoxybenzyl |
| 369 | CH₂—CH₂—C₂H₅ | 3-methoxybenzyl |
| 370 | CH₂—CH₂—C₂H₅ | 4-methoxybenzyl |
| 371 | CH(CH₃)₂ | CH₂CH₂—Cl |
| 372 | CH(CH₃)₂ | CH₂CH₂—CN |
| 373 | CH(CH₃)₂ | CH₂—CO—OCH₃ |
| 374 | CH(CH₃)₂ | CH₂—CO—OC₂H₅ |
| 375 | CH(CH₃)₂ | CH(CH₃)—CO—OCH₃ |
| 376 | CH(CH₃)₂ | CH₂CH₂—OCH₃ |
| 377 | CH(CH₃)₂ | CH(CH₃)₂ |
| 378 | CH(CH₃)₂ | CH(CH₃)—C₂H₅ |
| 379 | CH(CH₃)₂ | CH₂—CH(CH₃)₂ |
| 380 | CH(CH₃)₂ | C(CH₃)₃ |
| 381 | CH(CH₃)₂ | CH(CH₃)—CH₂—C₂H₅ |
| 382 | CH(CH₃)₂ | CH₂—CH(CH₃)—C₂H₅ |
| 383 | CH(CH₃)₂ | CH₂CH₂—CH(CH₃)₂ |
| 384 | CH(CH₃)₂ | CH₂—CH═CH₂ |
| 385 | CH(CH₃)₂ | CH(CH₃)═CH₂ |
| 386 | CH(CH₃)₂ | CH₂═CH—CH₃ |
| 387 | CH(CH₃)₂ | CH₂—C≡CH |
| 388 | CH(CH₃)₂ | CH(CH₃)—C≡CH |
| 389 | CH(CH₃)₂ | cyclopropyl |
| 390 | CH(CH₃)₂ | CH₂-cyclopropyl |
| 391 | CH(CH₃)₂ | cyclopentyl |
| 392 | CH(CH₃)₂ | CH₂-cyclopentyl |
| 393 | CH(CH₃)₂ | CH₂-(1,3-dioxolan-2-yl) |
| 394 | CH(CH₃)₂ | CH₂-(2-furyl) |
| 395 | CH(CH₃)₂ | CH₂-(3-furyl) |
| 396 | CH(CH₃)₂ | CH₂-(2-thienyl) |
| 397 | CH(CH₃)₂ | CH₂-(3-thienyl) |
| 398 | CH(CH₃)₂ | phenyl |
| 399 | CH(CH₃)₂ | 2-chlorophenyl |
| 400 | CH(CH₃)₂ | 3-chlorophenyl |
| 401 | CH(CH₃)₂ | 4-chlorophenyl |
| 402 | CH(CH₃)₂ | 2-fluorophenyl |
| 403 | CH(CH₃)₂ | 3-fluorophenyl |
| 404 | CH(CH₃)₂ | 4-fluorophenyl |
| 405 | CH(CH₃)₂ | 2-methylphenyl |
| 406 | CH(CH₃)₂ | 3-methylphenyl |
| 407 | CH(CH₃)₂ | 4-methylphenyl |
| 408 | CH(CH₃)₂ | 2-methoxyphenyl |
| 409 | CH(CH₃)₂ | 3-methoxyphenyl |
| 410 | CH(CH₃)₂ | 4-methoxyphenyl |
| 411 | CH(CH₃)₂ | 2-(methoxycarbonyl)phenyl |
| 412 | CH(CH₃)₂ | 3-(methoxycarbonyl)phenyl |
| 413 | CH(CH₃)₂ | 4-(methoxycarbonyl)phenyl |
| 414 | CH(CH₃)₂ | 2-nitrophenyl |
| 415 | CH(CH₃)₂ | 3-nitrophenyl |
| 416 | CH(CH₃)₂ | 4-nitrophenyl |
| 417 | CH(CH₃)₂ | 2-(dimethylamino)phenyl |
| 418 | CH(CH₃)₂ | 3-(dimethylamino)phenyl |
| 419 | CH(CH₃)₂ | 4-(dimethylamino)phenyl |
| 420 | CH(CH₃)₂ | 2-(trifluoromethyl)phenyl |
| 421 | CH(CH₃)₂ | 3-(trifluoromethyl)phenyl |
| 422 | CH(CH₃)₂ | 4-(trifluoromethyl)phenyl |
| 423 | CH(CH₃)₂ | 3-(phenoxy)phenyl |
| 424 | CH(CH₃)₂ | 4-(phenoxy)phenyl |
| 425 | CH(CH₃)₂ | 2,4-difluorophenyl |
| 426 | CH(CH₃)₂ | 2,4-dichlorophenyl |
| 427 | CH(CH₃)₂ | 3,4-difluorophenyl |
| 428 | CH(CH₃)₂ | 3,4-dichlorophenyl |
| 429 | CH(CH₃)₂ | 3,5-difluorophenyl |
| 430 | CH(CH₃)₂ | 3,5-dichlorophenyl |
| 431 | CH(CH₃)₂ | 2-pyridyl |
| 432 | CH(CH₃)₂ | 3-pyridyl |
| 433 | CH(CH₃)₂ | 4-pyridyl |
| 434 | CH(CH₃)₂ | α-naphthyl |
| 435 | CH(CH₃)₂ | benzyl |
| 436 | CH(CH₃)₂ | 2-chlorobenzyl |
| 437 | CH(CH₃)₂ | 3-chlorobenzyl |
| 438 | CH(CH₃)₂ | 4-chlorobenzyl |
| 439 | CH(CH₃)₂ | 2-methoxybenzyl |
| 440 | CH(CH₃)₂ | 3-methoxybenzyl |
| 441 | CH(CH₃)₂ | 4-methoxybenzyl |
| 442 | —(CH₂)₄— | |
| 443 | —CH₂—CH═CH—CH₂— | |
| 444 | H | cyclohexyl |
| 445 | CH₃ | cyclohexyl |
| 446 | C₂H₅ | cyclohexyl |
| 447 | n-C₃H₇ | cyclohexyl |
| 448 | i-C₃H₇ | cyclohexyl |
| 449 | n-C₄H₉ | cyclohexyl |
| 450 | i-C₄H₉ | cyclohexyl |
| 451 | sec-C₄H₉ | cyclohexyl |
| 452 | tert-C₄H₉ | cyclohexyl |
| 453 | H | CH₂—CH═CH—CH₃ |
| 454 | CH₃ | CH₂—CH═CH—CH₃ |
| 455 | C₂H₅ | CH₂—CH═CH—CH₃ |
| 456 | n-C₃H₇ | CH₂—CH═CH—CH₃ |
| 457 | i-C₃H₇ | CH₂—CH═CH—CH₃ |
| 458 | n-C₄H₉ | CH₂—CH═CH—CH₃ |
| 459 | i-C₄H₉ | CH₂—CH═CH—CH₃ |
| 460 | sec-C₄H₉ | CH₂—CH═CH—CH₃ |
| 461 | tert-C₄H₉ | CH₂—CH═CH—CH₃ |
| 462 | H | CH₃S—CH₂CH₂ |
| 463 | CH₃ | CH₃S—CH₂CH₂ |
| 464 | C₂H₅ | CH₃S—CH₂CH₂ |
| 465 | n-C₃H₇ | CH₃S—CH₂CH₂ |
| 466 | i-C₃N₇ | CH₃S—CH₂CH₂ |
| 467 | n-C₄H₉ | CH₃S—CH₂CH₂ |
| 468 | i-C₄H₉ | CH₃S—CH₂CH₂ |
| 469 | sec-C₄H₉ | CH₃S—CH₂CH₂ |
| 470 | tert-C₄H₉ | CH₃S—CH₂CH₂ |
| 471 | H | C₂H₅—O—CH₂CH₂ |
| 472 | CH₃ | C₂H₅—O—CH₂CH₂ |
| 473 | C₂H₅ | C₂H₅—O—CH₂CH₂ |
| 474 | n-C₃H₇ | C₂H₅—O—CH₂CH₂ |
| 475 | i-C₃H₇ | C₂H₅—O—CH₂CH₂ |
| 476 | n-C₄H₉ | C₂H₅—O—CH₂CH₂ |
| 477 | i-C₄H₉ | C₂H₅—O—CH₂CH₂ |
| 478 | sec-C₄H₉ | C₂H₅—O—CH₂CH₂ |
| 479 | tert-C₄H₉ | C₂H₅—O—CH₂CH₂ |
| 480 | CH₂CH₂—O—CH₂CH₂ | |
| 481 | CH₂—CH═CH—CH₂ | |
| 482 | CH═CH—CH₂—CH₂ | |

TABLE 1-continued

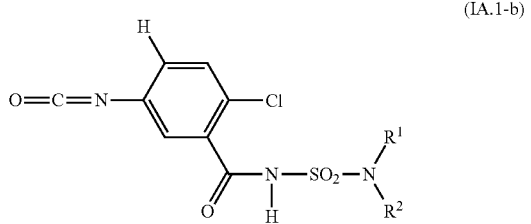

(IA.1-a)

| No. | R¹ | R² |
|---|---|---|
| 483 | $CH_2-CH_2-CH_2-CH_2-CH_2$ | |
| 484 | $CH_2-CH_2-O-CH(CH_3)-CH_2$ | |
| 485 | $CH_2-CH_2-O-CH_2-CH(CH_3)$ | |
| 486 | $CH_2-CH_2-N(CH_3)-CH_2-CH_2$ | |
| 487 | $CH_2-CH(CH_3)-O-CH(CH_3)-CH_2$ | |
| 488 | $CH_2-CH=CH-CH_2-CH_2$ | |
| 489 | $CH=CH-CH_2-CH_2-CH_2$ | |
| 490 | $CH_2-CH_2-CH_2-CH_2-CH(CH_3)$ | |
| 491 | $CH_2-CH_2-CH_2-CH(CH_3)-CH_2$ | |
| 492 | $CH_2-CH_2-CH(CH_3)-CH_2-CH_2$ | |
| 493 | $CH_2-CH_2-CH_2-CH_2-CH(CH_2CH_2Cl)$ | |
| 494 | $CH_2-CH_2-CH_2-CH(CH_2CH_2Cl)-CH_2$ | |
| 495 | $CH_2-CH_2-CH(CH_2CH_2Cl)-CH_2-CH_2$ | |

Very particular preference is given to the isocyanatobenzoylsulfamic acid amides of the formula IA.1-b (≡I where W=oxygen, Ar=Ar-1 where $R^a$=Cl and $R^b$=$R^d$=hydrogen and $R^c$=H, A=$NR^1R^2$), where $R^1$, $R^2$ have the meanings mentioned above, and in particular the meanings mentioned as being preferred. Examples of such compounds are the compounds IA.1-b.1 to IA.1-b.495 in which the variables $R^1$, $R^2$ together have the meanings given in one row of Table 1.

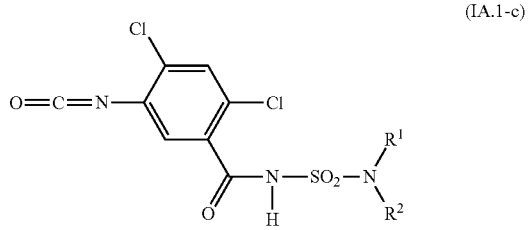

(IA.1-b)

Very particular preference is given to the isocyanatobenzoylsulfamic acid amides of the formula IA.1-c (≡I where W=oxygen, Ar=Ar-1 where $R^a$=Cl and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds IA.1-c.1 to IA.1-c.495 in which the variables $R^1$, $R^2$ together have the meanings given in one row of Table 1.

(IA.1-c)

Very particular preference is given to the isocyanatobenzoylsulfamic acid amides of the formula IA.1-d (≡I where W=oxygen, Ar=Ar-1 where $R^a$=F and $R^b$=$R^d$=hydrogen and $R^c$=F, A=$NR^1R^2$) where $R^1$, $R^2$ have the meanings mentioned above, and in particular the meanings mentioned as being preferred. Examples of such compounds are the compounds IA.1-d.1 to IA.1-d.495 in which the variables $R^1$, $R^2$ together have the meanings given in one row of Table 1.

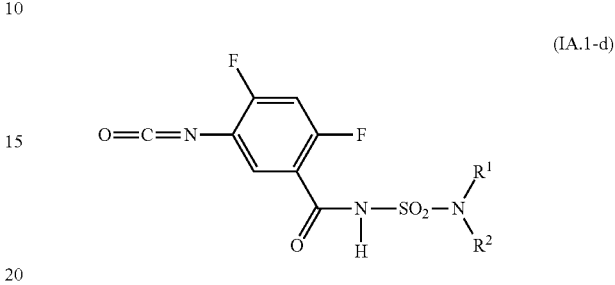

(IA.1-d)

Very particular preference is given to the isocyanatobenzoylsulfamic acid amides of the formula IA.1-e (≡I where W=oxygen, Ar=Ar-1 where $R^a$=CN and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds IA.1-e.1 to IA.1-e.495 in which the variables $R^1$, $R^2$ together have the meanings given in one row of Table 1.

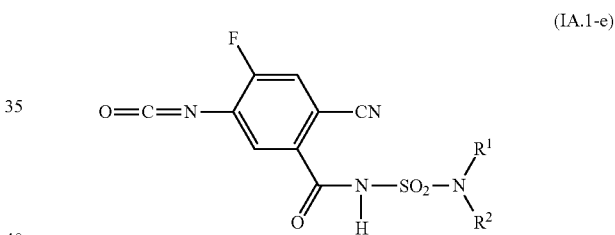

(IA.1-e)

Very particular preference is given to the isocyanatobenzoylsulfamic acid amides of the formula IA.1-f (≡I where W=oxygen, Ar=Ar-1 where $R^a$=CN and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds IA.1-f.1 to IA.1-f.495 in which the variables $R^1$, $R^2$ together have the meanings given in one row of Table 1.

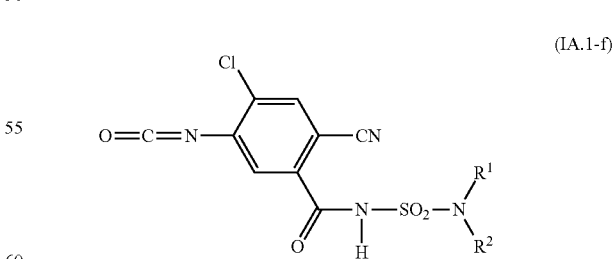

(IA.1-f)

Very particular preference is given to the isothiocyanatobenzoylsulfamic acid amides of the formula IA.1-g (≡I where W=sulfur, Ar=Ar-1 where $R^a$=Cl and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds IA.1-g.1 to IA.1-g.495 in which the variables $R^1$, $R^2$ together have the meanings given in one row of Table 1.

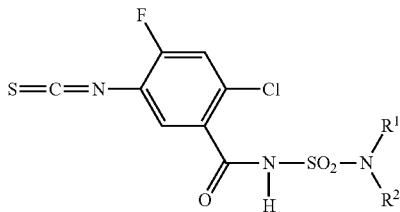

(IA.1-g)

Very particular preference is given to the isothiocyanato-benzoylsulfamic acid amides of the formula IA.1-h (≡I where W=sulfur, Ar=Ar-1 where $R^a$=Cl and $R^b$=$R^d$=hydrogen and $R^c$=H, A=$NR^1R^2$), where $R^1$, $R^2$ have the meanings mentioned above, and in particular the meanings mentioned as being preferred. Examples of such compounds are the compounds IA.1-h.1 to IA.1-h.495 in which the variables $R^1$, $R^2$ together have the meanings given in one row of Table 1.

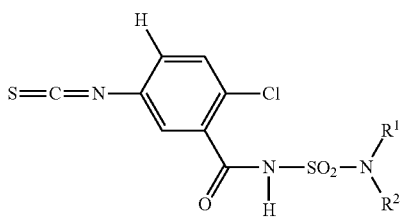

(IA.1-h)

Very particular preference is given to the isothiocyanato-benzoylsulfamic acid amides of the formula IA.1-i (≡I where W=sulfur, Ar=Ar-1 where $R^a$=Cl and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds IA.1-i.1 to IA.1-i.495 in which the variables $R^1$, $R^2$ together have the meanings given in one row of Table 1.

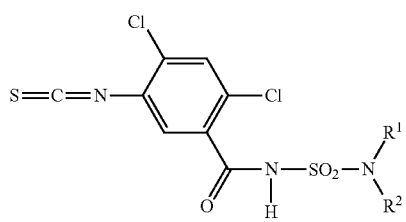

(IA.1-i)

Very particular preference is given to the isothiocyanato-benzoylsulfamic acid amides of the formula IA.1-j (≡I where W=sulfur, Ar=Ar-1 where $R^a$=F and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds IA.1-j.1 to IA.1-j.495 in which the variables $R^1$, $R^2$ together have the meanings given in one row of Table 1.

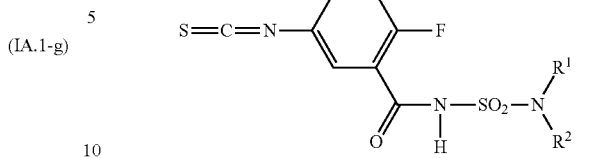

(IA.1-j)

Very particular preference is given to the isothiocyanato-benzoylsulfamic acid amides of the formula IA.1-k (≡I where W=sulfur, Ar=Ar-1 where $R^a$=CN and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds IA.1-k.1 to IA.1-k.495 in which the variables $R^1$, $R^2$ together have the meanings given in one row of Table 1.

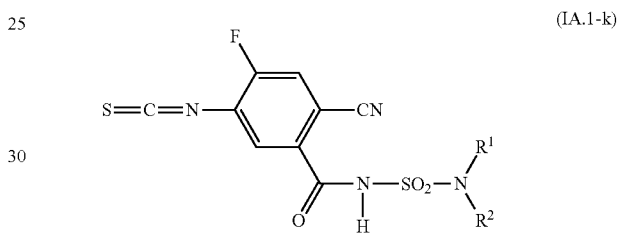

(IA.1-k)

Very particular preference is given to the isothiocyanatobenzoylsulfamic' acid amides of the formula IA.1-1 (≡I where W=sulfur, Ar=Ar-1 where $R^a$=CN and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds IA.1-1.1 to IA.1-1.495 in which the variables $R^1$, $R^2$ together have the meanings given in one row of Table 1.

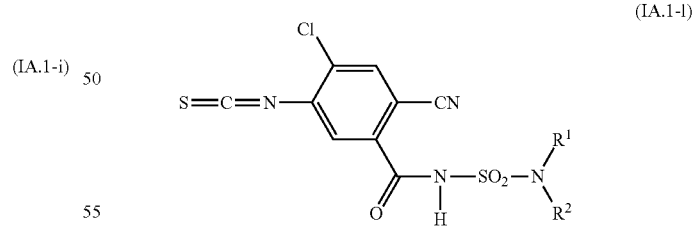

(IA.1-l)

In the process according to the invention, the starting materials used are aminobenzoylsulfamic acid amides of the formula II. These compounds are likewise novel and represent useful intermediates for preparing the iso(thio)cyanatobenzoylsulfamic acid amides I. With respect to the preparation process, reference is made to what has been said above.

Accordingly, the present invention also relates to the aniline compounds of the formula II, in particular to compounds of the formula IIA (≡I where Ar=Ar-1),

IIA

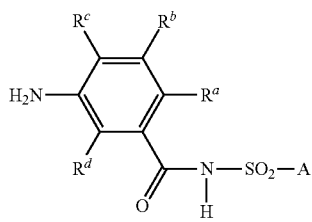

where $R^a$, $R^b$, $R^c$, $R^d$ and A are as defined above. In the formula IIA, $R^a$, $R^b$, $R^c$, $R^d$ and A preferably denote those radicals which have already been mentioned in connection with the description of the compounds I according to the invention as being preferred for these variables.

Particular preference is given to the compounds of the formula IIA.1, (IIA.1)

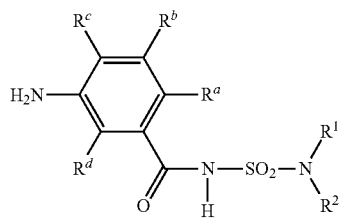

in which the variables $R^{11}$, $R^2$, $R^a$, $R^b$, $R^e$, $R^d$ are as defined above. In the formula IIA.1, the variables $R^1$, $R^2$, $R^a$, $R^b$, $R^e$, $R^d$ preferably have those meanings which have already been mentioned in connection with the description of the compounds IA.1 according to the invention as being preferred.

Very particular preference is given to the aminobenzoyl-sulfamic acid amides of the formula IIA.1-a (≡II where Ar=Ar-1 where $R^a$=Cl and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds IIA.1-a.1 to IIA.1-a.495 in which the variables $R^1$, $R^2$ together have the meanings given in one row of Table 1.

(IIA.1-a)

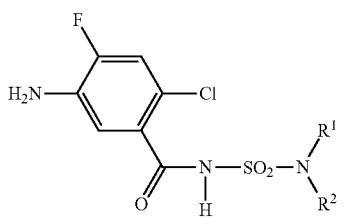

Very particular preference is given to the aminobenzoyl-sulfamic acid amides of the formula IIA.1-b (≡II where Ar=Ar-1 where $R^a$=Cl and $R^b$=$R^d$=hydrogen and $R^c$=H, A=$NR^1R^2$), where $R^1$, $R^2$ have the meanings mentioned above, and in particular the meanings mentioned as being preferred. Examples of such compounds are the compounds IIA.1-b.1 to IIA.1-b.495 in which the variables $R^1$, $R^2$ together have the meanings given in one row of Table 1.

(IIA.1-b)

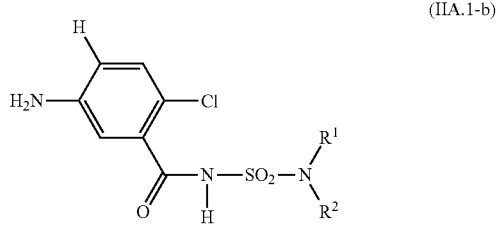

Very particular preference is given to the aminobenzoyl-sulfamic acid amides of the formula IIA.1-c (≡II where Ar=Ar-1 where $R^a$=Cl and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds IIA.1-c.1 to IIA.1-c.495 in which the variables $R^1$, $R^2$ together have the meanings given in one row of Table 1.

(IIA.1-c)

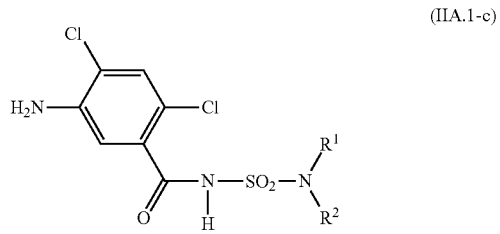

Very particular preference is given to the aminobenzoyl-sulfamic acid amides of the formula IIA.1-d (m II where Ar=Ar-1 where $R^a$=F and $R^b$=$R^d$=hydrogen and $R^c$=F, A=$NR^1R^2$) where $R^1$, $R^2$ have the meanings mentioned above, and in particular the meanings mentioned as being preferred. Examples of such compounds are the compounds IIA.1-d.1 to IIA.1-d.495 in which the variables $R^1$, $R^2$ together have the meanings given in one row of Table 1.

(IIA.1-d)

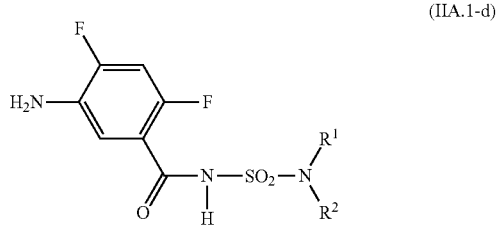

Very particular preference is given to the aminobenzoyl-sulfamic acid amides of the formula IIA.1-e (≡II where Ar=Ar-1 where $R^a$=CN and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds IIA.1-e.1 to IIA.1-e.495 in which the variables $R^1$, $R^2$ together have the meanings given in one row of Table 1.

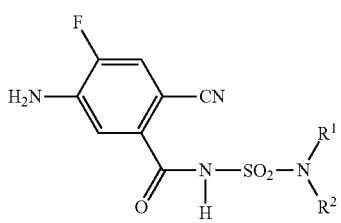
(IIA.1-e)

Very particular preference is given to the aminobenzoylsulfamic acid amides of the formula IIA.1-f (≡II where Ar=Ar-1 where $R^a$=CN and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds IIA.1-f.1 to IIA.1-f.495 in which the variables $R^1$, $R^2$ together have the meanings given in one row of Table 1.

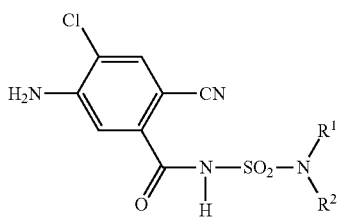
(IIA.1-f)

The nitrobenzoylsulfamic acid amides of the formula V are likewise novel and also represent useful intermediates for preparing the iso(thio)cyanatobenzoylsulfamic acid amides I. They also form part of the subject-matter of the present invention.

Accordingly, the present invention also relates to the nitro compounds of the formula V, in particular to compounds of the formula VA (≡V where Ar=Ar-1),

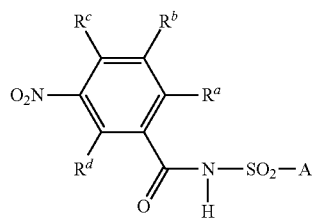
VA where $R^a$, $R^b$, $R^c$, $R^d$ and A are as defined above. In the formula VA, $R^a$, $R^b$, $R^c$, $R^d$ and A preferably denote those radicals which have already been mentioned in connection with the description of the compound I according to the invention as being preferred for these variables.

Very particular preference is given to the compounds of the formula VA.1,

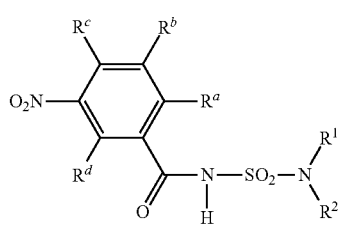
(VA.1)

in which the variables $R^1$, $R^2$, $R^a$, $R^b$, $R^c$, $R^d$ are as defined above. In the formula VA.1, the variables $R^1$, $R^2$, $R^a$, $R^b$, $R^c$, $R^d$ preferably have those meanings which have already been mentioned in connection with the description of the compounds IA.1 according to the invention as being preferred.

Very particular preference is given to the nitrobenzoylsulfamic acid amides of the formula VA.1-a V where Ar=Ar-1 where $R^a$=Cl and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds VA.1-a.1 to VA.1-a.495 in which the variables $R^1$, $R^2$ together have the meanings given in one row of Table 1.

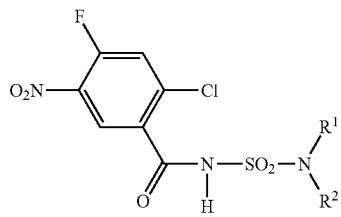
(VA.1-a)

Very particular preference is given to the nitrobenzoylsulfamic acid amides of the formula VA.1-b (≡V where Ar=Ar-1 where $R^a$=Cl and $R^b$=$R^d$=hydrogen and $R^c$=H, A=$NR^1R^2$), where $R^1$, $R^2$ have the meanings mentioned above, and in particular the meanings mentioned as being preferred. Examples of such compounds are the compounds VA.1-b.1 to VA.1-b.495 in which the variables $R^1$, $R^2$ together have the meanings given in one row of Table 1.

(VA.1-b)

Very particular preference is given to the nitrobenzoylsulfamic acid amides of the formula VA.1-c (≡V where Ar=Ar-1 where $R^a$=Cl and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds VA.1-c.1 to VA.1-c.495 in which the variables $R^1$, $R^2$ together have the meanings given in one row of Table 1.

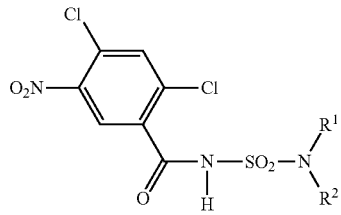
(VA.1-c)

Very particular preference is given to the nitrobenzoylsulfamic acid amides of the formula VA.1-d (m V where Ar=Ar-1 where $R^a$=F and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds VA.1-d.1 to VA.1-d.495 in which the variables $R^1$, $R^2$ together have the meanings given in one row of Table 1.

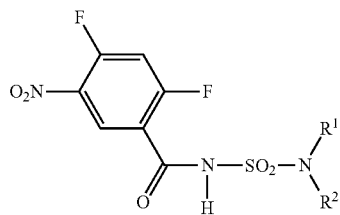

(VA.1-d)

Very particular preference is given to the nitrobenzoylsulfamic acid amides of the formula VA.1-e (≡V where Ar=Ar-1 where $R^a$=CN and $R^b$=$R^d$=hydrogen and $R^c$=F, A=$NR^1R^2$), where $R^1$, $R^2$ have the meanings mentioned above, and in particular the meanings mentioned as being preferred. Examples of such compounds are the compounds VA.1-e.1 to VA.1-e.495 in which the variables $R^1$, $R^2$ together have the meanings given in one row of Table 1.

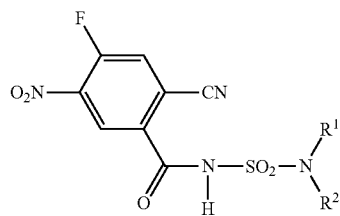

(VA.1-e)

Very particular preference is given to the nitrobenzoylsulfamic acid amides of the formula VA.1-f V where Ar=Ar-1 where $R^a$=CN and $R^b$=$R^d$=hydrogen and $R^c$=Cl, A=$NR^1R^2$), where $R^1$, $R^2$ have the meanings mentioned above, and in particular the meanings mentioned as being preferred. Examples of such compounds are the compounds VA.1-f.1 to VA.1-f.495 in which the variables $R^1$, $R^2$ together have the meanings given in one row of Table 1.

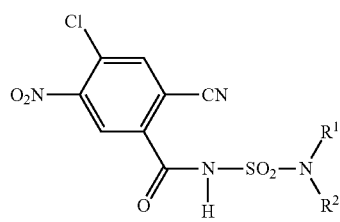

(VA.1-f)

The bifunctional phenyl iso(thio)cyanates I according to the invention can be used as starting materials for pharmacologically active compounds or crop protection agents. WO 01/83459, for example, describes herbicidal 3-(triazolidinedione)-substituted benzoic acid sulfamoyl amides of the formula below

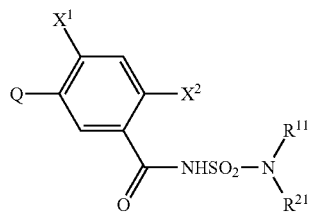

where $X^1$ is hydrogen, halogen, $C_1$-$C_4$-alkyl, $X^2$ is hydrogen, CN, CS—$NH_2$, halogen, $C_1$-$C_4$-alkyl, $C_1$-$C_4$-haloalkyl, $R^{11}$ and $R^{21}$ have the meanings given above for $R^1$ and $R^2$, respectively, and are in particular hydrogen, unsubstituted or substituted hydroxyl, $C_1$-$C_{10}$-alkyl, $C_2$-$C_{10}$-alkenyl, $C_3$-$C_{10}$-alkynyl, $C_3$-$C_7$-cycloalkyl, phenyl, benzyl or $C_5$-$C_7$-cycloalkenyl, or $R^{11}$ and $R^{21}$ together with the nitrogen atom to which they are attached form a 3- to 7-membered heterocyclic ring, and Q is a radical of the formula a

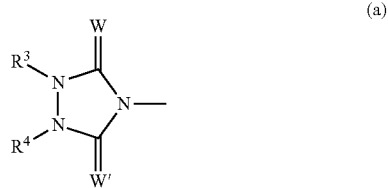

(a)

where W is as defined above, W' is O or S and $R^3$ and $R^4$ independently of one another are one of the radicals below: hydrogen, cyano, amino, $C_1$-$C_6$-alkyl, $C_1$-$C_6$-haloalkyl, $C_1$-$C_6$-haloalkoxy, $C_3$-$C_7$-cycloalkyl, $C_2$-$C_6$-alkenyl, $C_2$-$C_6$-haloalkenyl, $C_3$-$C_6$-alkynyl, benzyl, $OR^5$ (where $R^5$ is hydrogen, $C_1$-$C_6$-alkyl, $C_1$-$C_6$-haloalkyl, $C_3$-$C_7$-cycloalkyl, $C_2$-$C_6$-alkenyl, $C_3$-$C_6$-alkynyl, unsubstituted or substituted phenyl or unsubstituted or substituted benzyl), $C_1$-$C_3$-cyanoalkyl, or $R^3$ and $R^4$ together with the nitrogen atoms to which they are attached form a four- to seven-membered heterocycle which is optionally interrupted by sulfur, oxygen, a group $NR^6$ (where $R^6$ is as defined above) or nitrogen and which is unsubstituted or mono- or polysubstituted by halogen or $C_1$-$C_4$-alkyl, and is in particular a radical of the formula b:

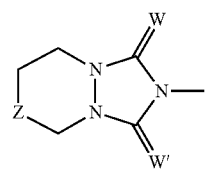

(b)

where W is as defined above and W' and Z independently of one another are oxygen or sulfur.

The herbicides described in WO 01/83459 are not always obtainable in sufficient yields and purity. The processes described therein are based, for example:

A) on the condensation of a substituted benzoic acid with a substituted sulfamic acid amide in the presence of N,N-carbonyldiimidazole (CDI) or the conversion of the carboxylic acid into its acid chloride and subsequent reaction of the acid chloride with the sulfamic acid amide.

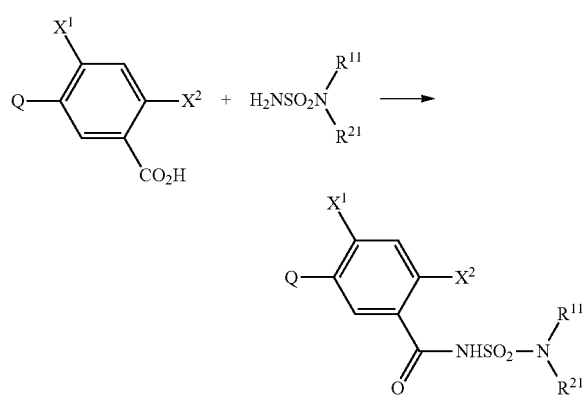

Here, the variables $R^{11}$, $R^{21}$, $X^1$ and $X^2$ may have the meanings mentioned above, and Q is a 5- or 6-membered heterocycle, for example a radical a or b.

This process has the disadvantage that the benzoic acid used can only be obtained from the ester precursor by cleavage with boron tribromide, with the corresponding amount of salt being produced. Moreover, the yield of the condensation with sulfamic acid amides is only from 16 to 45%. Even the detour via an acid chloride, prepared beforehand, gives the desired benzoylsulfamic acid amide in a yield of only 26%, and in addition, its impurities have to be removed chromatographically.

B) The substitution of a halogen radical by the heterocyclic radical Q:

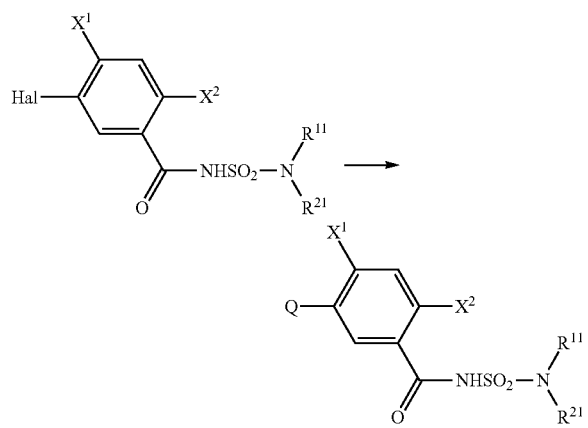

Here, the variables $R^{11}$, $R^{21}$, $X^1$ and $X^2$ may have the meanings mentioned above, Hal is fluorine, chlorine or bromine and Q is a 5- or 6-membered heterocycle, for example a radical a or b.

This process has the disadvantages that the halogenated aromatic compound used has to be provided in a complicated manner via a Sandmeyer reaction, and moreover an unsatisfactory selectivity in the reaction of the 5-halo-substituted compound, compared to the—activated—2,4-dihalosubstituents present in the same molecule.

Accordingly, all of the prior-art processes for preparing 3-(triazolidinedione)-substituted benzoylsulfamoylamides and their sulfur analogs are unsatisfactory with respect to a short reaction time, a simple practice of the reaction, yields and purity of the end products, and are therefore uneconomical.

Accordingly, it is another object of the present invention to provide a process for preparing compounds of the formula VI,

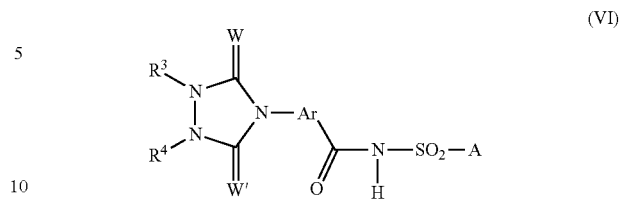

(VI)

where W, Ar and A are as defined in claim 1, W' is O or S and $R^3$ and $R^4$ independently of one another are hydrogen, cyano, amino, $C_1$-$C_6$-alkyl, $C_1$-$C_6$-haloalkyl, $C_1$-$C_6$-haloalkoxy, $C_3$-$C_7$-cycloalkyl, $C_2$-$C_6$-alkenyl, $C_2$-$C_6$-haloalkenyl, $C_3$-$C_6$-alkynyl, benzyl, $OR^5$ (where $R^5$ is hydrogen, $C_1$-$C_6$-alkyl, $C_1$-$C_6$-haloalkyl, $C_3$-$C_7$-cycloalkyl, $C_2$-$C_6$-alkenyl, $C_3$-$C_6$-alkynyl, unsubstituted or substituted phenyl or unsubstituted or substituted benzyl), $C_1$-$C_3$-cyanoalkyl, or $R^3$ and $R^4$ together with the nitrogen atoms to which they are attached form a four- to seven-membered heterocycle which is optionally interrupted by sulfur, oxygen, a group $NR^6$ (where $R^6$ is as defined above) or nitrogen and which is unsubstituted or mono- or polysubstituted by halogen or $C_1$-$C_4$-alkyl.

Surprisingly, it has now been found that, starting with the compounds of the formula I according to the invention, in particular the compounds of the formula IA, it is possible to prepare the compounds of the formula VI described in WO 01/83459 in a much more simple manner, without side reactions and in higher yields and purity.

Accordingly, the present invention also provides a process for preparing compounds of the formula VI

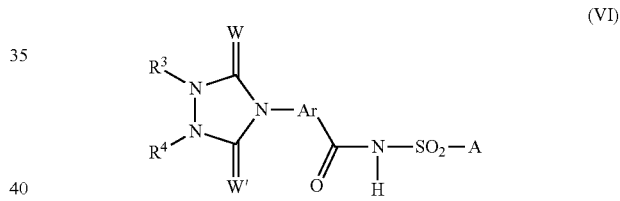

(VI)

where $R^3$, $R^4$, W, W', Ar, A are as defined above
which comprises the following steps
(i) reaction of a compound of the formula I as defined above with an oxadiazinecarboxylic acid ester of the formula VII,

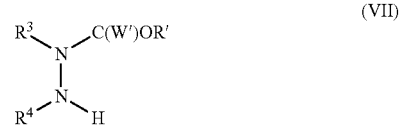

(VII)

where W' is as defined above and R' is $C_1$-$C_4$-alkyl, giving a urea derivative of the formula VIII

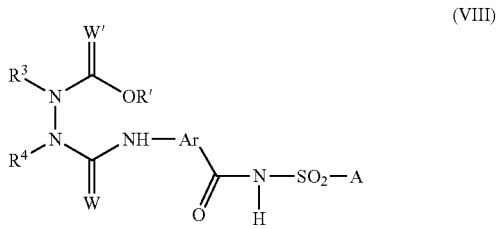

(VIII)

where the variables $R^3$, $R^4$, R', W, W', Ar and A are as defined above, and
(ii) cyclization of the resulting intermediate VIII, giving a compound of the formula VI.

Step (i) is carried out in a manner known per se, for example as described in WO 02/20531. In general, the iso(thio)cyanate of the formula I according to the invention is added to a compound of the formula VII, preferably in a solvent. Suitable solvents are hydrocarbons, such as pentane, hexane, cyclopentane, cyclohexane, toluene, xylene; chlorinated hydrocarbons, such as methylene chloride, chloroform, 1,2-dichloroethane, 1,1,2,2-tetrachloroethane, chlorobenzene, 1,2-, 1,3- or 1,4-dichlorobenzene; ethers, such as 1,4-dioxane, anisole; glycol ethers, such as dimethyl glycol ether, diethyl glycol ether, diethylene glycol dimethyl ether; esters, such as ethyl acetate, propyl acetate, methyl isobutyrate, isobutyl acetate; carboxamides, such as N,N-dimethylformamide, N-methylpyrrolidone; nitrated hydrocarbons, such as nitrobenzene, nitriles, such as acetonitrile, propionitrile, butyronitrile or isobutyronitrile; or else mixtures of individual solvents. The addition is generally carried out over a period of from 5 to 30 minutes. During the addition, the temperature is usually from 10 to 25° C. To bring the reaction to completion, the mixture is stirred for another 0.5 to 24 hours at from 20 to 80° C. It is, of course, also possible to initially charge the iso(thio)cyanate I in one of the abovementioned solvents, to add the compound VII and then to bring the reaction to completion as described above. Usually, from 0.9 to 1.4 mol, preferably from 0.95 to 1.1 mol and particularly preferably from 0.98 to 1.15 mol of the compound VII are employed per mole of the compound I. The compound of the formula VII used in step (i) is known or can be prepared similarly to the process described in WO 02/20531.

Step (ii) is again carried out in a manner known per se, for example as described in WO 02/20531, by treating the compound of the formula VIII with a base.

Suitable bases are, in principle, all compounds capable of abstracting the acidic proton of the NH group of the urea function in the compounds of the formula VIII. These include oxo bases, nitrogen bases and hydride bases.

The oxo bases include, for example, inorganic bases, such as alkali metal or alkaline earth metal hydroxides, alkali metal or alkaline earth metal bicarbonates, and also alkali metal and alkaline earth metal carbonates, for example lithium hydroxide, bicarbonate or carbonate, sodium hydroxide, bicarbonate or carbonate, potassium hydroxide, bicarbonate or carbonate, calcium hydroxide, bicarbonate or carbonate, or magnesium hydroxide, bicarbonate or carbonate. Suitable oxo bases are likewise alkali metal alkoxides, in particular those of lithium, sodium or potassium, where, in general, alkoxides of $C_1$-$C_6$-, preferably $C_1$-$C_4$-alkanols, such as sodium methoxide, ethoxide, n-butoxide or tert-butoxide or potassium methoxide, ethoxide, n-butoxide or tert-butoxide are used. The nitrogen bases include primary, secondary or, preferably, tertiary amines, for example trialkylamines, such as triethylamine, tri-n-propylamine, N-ethyldiisopropylamine; cycloaliphatic amines, such as N,N-dimethylcyclohexylamine; cyclic amines, such as azabicyclo[2.2.2]octane (=triethylenediamine), N-methylpyrrolidine, N-ethylpiperidine; dialkylanilines, such as dimethylaminoaniline; p-dimethylaminopyridine; furthermore aromatic nitrogen heterocycles, such as pyridine, α-, β- or γ-picoline, 2,4- and 2,6-lutidine, quinoline, quinazoline, quinoxaline, pyrimidine; and also tertiary amides, for example dimethylformamide, N-methylformamide, N-methylpyrrolidone or tetramethylurea.

Suitable hydride bases are, for example, alkali metal hyrides, such as sodium hydride or potassium hydride. Preferred bases are tertiary amines, in particular trialkylamines.

Preference is given to using from 0.9 to 1.4 mol, in particular from 0.95 to 1.2 mol and with particular preference from 0.98 to 1.15 mol of the compound VIII per mole of base.

For the reaction of the compound VIII with the base, the compound VIII is preferably initially charged in one of the solvents mentioned above or in a solvent mixture, and the base is added with mixing, for example with stirring, to the reaction mixture. The addition of the base is preferably carried out at a temperature in the range from 0 to 50° C. and in particular from 10 to 30° C.

In general, the components are then allowed to react for another 10 minutes to 48 hours at from 20 to 150° C., preferably from 20 to 100° C. and in particular from 20 to 60° C., to bring the reaction to completion. In the case of thioureas of the formula VIII (W=S), the reaction is generally substantially complete (conversion>90%) after 0.5-10 hours, and in the case ureas of the formula VIII (W=O) after 4-48 hours and in particular after 8-24 hours. However, it is also possible to initially charge the base, preferably in one of the solvents mentioned above, followed by addition of the compound VIII and conclusion of the reaction as above.

The concentration of the starting materials in the solvent is generally in the range from 0.5 to 5 mol/l, preferably in the range from 0.2 to 2 mol/l.

Work-up of the reaction is carried out in a customary manner, for example by aqueous extraction, by dialysis and/or chromatographically.

The present process relates in particular to the preparation of compounds VIA

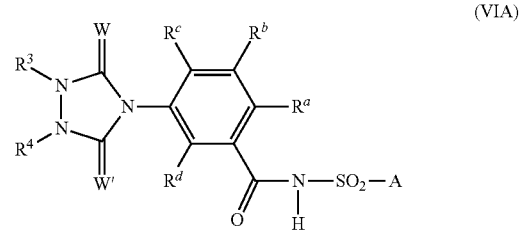

(VIA)

where $R^3$ and $R^4$ are as defined above and the variables W, W', $R^a$, $R^b$, $R^c$, $R^d$, A have the meanings given above and in particular the meanings which have already been mentioned in connection with the description of compound IA as being preferred for these variables. In this case, the compound used in the process according to the invention for preparing the compound VIA is a compound of the formula IA, preferably a compound of the formula IA.1.

A preferred compound of the formula VII is, for example, a compound of the formula (VII')

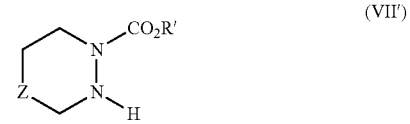

(VII')

where Z is O or S and R' is $C_1$-$C_4$-alkyl. This compound is known from WO 02/20531.

By this route, starting with the compounds of the formula IA, it is possible, in accordance with Scheme 3 below, to prepare in particular compounds of the formula IX (=compound VIA where $R^b$=$R^d$=H, A=$NR^1R^2$, W=W'=O and $R^3$, $R^4$ are $CH_2CH_2OCH_2$).

Scheme 3:

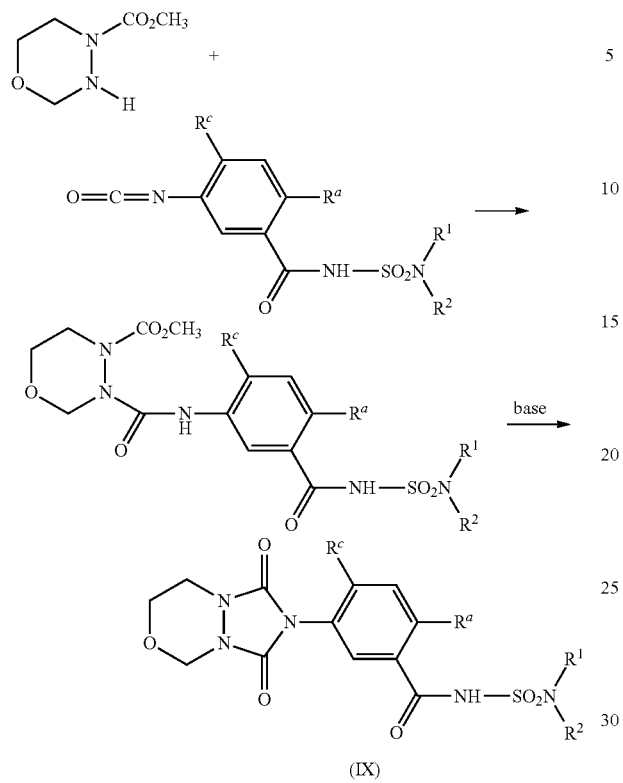

Here, the variables $R^a$, $R^c$, $R^1$ and $R^2$ have the meanings mentioned above.

The process according to the invention is, with respect to yields and purity, superior to the process described in WO 01/83459. Moreover, its practice is much easier. With respect to the disadvantages of the process known from WO 01/83459, reference is made to what has been said above.

The examples below serve to illustrate the invention

I Preparation of the nitrobenzoylsulfamic acid amides (intermediate of the formula VA.1; intermediates VA.1-1 to VA.1-24):

EXAMPLE 1

N-(2-Chloro-4-fluoro-5-nitrobenzoyl)-N'-n-propyl-N'-allyl-sulfamide (VA.1-a.241)

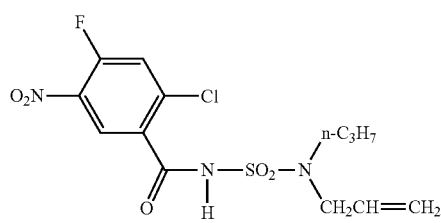

At from −5° C. to 0° C., 11.62 g (0.0474 mol) of 2-chloro-4-fluoro-5-nitrobenzoyl chloride in 50 ml methylene chloride were added with stirring, over 30 minutes, to a mixture of 8.50 g (0.048 mol) of N'-propyl-N'-allylsulfamide, 10.38 g (0.103 mol) of triethylamine and 0.09 g (0.736 mmol) of 4-N,N-dimethylaminopyridine in 90 ml of methylene chloride. The funnel was rinsed with 10 ml of the solvent. The mixture was initially stirred at 0° C. for 1 hour and then at 22° C. for 2 hours. 50 ml of 1N hydrochloric acid were then added, the mixture was stirred and the phases were separated. The organic phase was washed two more times with 1N hydrochloric acid and the aqueous phase was extracted with methylene chloride. Drying of the organic phase over magnesium sulfate was followed by filtration and concentration of the solution. The residue was triturated with diethyl ether/pentane, filtered off with suction and dried, giving 18.41 g (91.9% of theory) of the title compound of melting point (m.p.) of 110-112° C.

The intermediates VA.1 (compounds of the formula VI where Ar=Ar-1 where $R^b$, $R^d$=H and $R^1$ and $R^2$ have the meanings given in Table 1) of Examples 2 to 24 listed in Table 2 were obtained in an analogous manner.

TABLE 2

(VA.1)

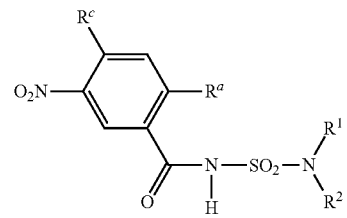

| Example/ No. [1] | $R^c$ | $R^a$ | $R^1$ | $R^2$ | m.p. [° C.]/ $^1$H-NMR (400 MHz, $CDCl_3$) δ (ppm) |
|---|---|---|---|---|---|
| 1 VA.1-a.241 | F | Cl | n-$C_3H_7$ | $CH_2$=CH—$CH_2$ | 110-112 |
| 2 VA.1-a.490 | F | Cl | $CH_2$—$CH_2$—CH($CH_3$)—$CH_2$—$CH_2$ | | 137-138 |
| 3 VA.1-a.387 | F | Cl | i-$C_3H_7$ | HC≡C—$CH_2$ | 160-161 |
| 4 VA.1-b.492 | H | Cl | $CH_2$—$CH_2$—CH($CH_3$)—$CH_2$—$CH_2$ | | 151-152 |
| 5 VA.1-b.241 | H | Cl | n-$C_3H_7$ | $CH_2$=CH—CH | 132-134 |
| 6 VA.1-b.387 | H | Cl | i-$C_3H_7$ | HC≡C—$CH_2$ | 138-140 |
| 7 VA.1-a.86 | F | Cl | $CH_3$ | i-$C_3H_7$ | 121-122 |
| 8 VA.1-a.76 | F | Cl | $CH_3$ | $CH_3$ | |
| 9 VA.1-a.77 | F | Cl | $CH_3$ | $C_2H_5$ | |
| 10 VA.1-a.84 | F | Cl | $CH_3$ | n-$C_3H_7$ | |
| 11 VA.1-a.98 | F | Cl | $CH_3$ | c-$C_3H_5$ | |
| 12 VA.1-a.85 | F | Cl | $CH_3$ | n-$C_4H_9$ | |
| 13 VA.1-a.88 | F | Cl | $CH_3$ | i-$C_4H_9$ | |
| 14 VA.1-a.87 | F | Cl | $CH_3$ | sec-$C_4H_9$ | |
| 15 VA.1-a.89 | F | Cl | $CH_3$ | tert-$C_4H_9$ | |
| 16 VA.1-a.93 | F | Cl | $CH_3$ | $CH_2$=CH—$CH_2$ | |
| 17 VA.1-a.96 | F | Cl | $CH_3$ | HC≡C—$CH_2$ | |
| 18 VA.1-a.107 | F | Cl | $CH_3$ | $C_6H_5$ | |

TABLE 2-continued (VA.1)

[Structure: 4-nitro, Rc-substituted benzene with Ra, connected to C(=O)-N(H)-SO2-N(R1)(R2)]

| Example/ No.[1) | $R^c$ | $R^a$ | $R^1$ | $R^2$ | m.p. [°C.]/ $^1$H-NMR (400 MHz, CDCl$_3$) δ (ppm) |
|---|---|---|---|---|---|
| 19 VA.1-a.445 | F | Cl | CH$_3$ | cyclohexyl | |
| 20 VA.1-a.181 | F | Cl | C$_2$H$_5$ | C$_6$H$_5$ | |
| 21 VA.1-a.446 | F | Cl | C$_2$H$_5$ | cyclohexyl | |
| 22 VA.1-a.160 | F | Cl | C$_2$H$_5$ | i-C$_3$H$_7$ | |
| 23 VA.1-a.167 | F | Cl | C$_2$H$_5$ | CH$_2$=CH—CH$_2$ | |
| 24 VA.1.-b.87 | H | Cl | CH$_3$ | sec.-C$_4$H$_9$ | 8.4 (d, 1H), 8.2 (m, 1H), 7.6 (d, 1H), 4.0 (sept., 1H), 2.9 (s, 3H), 1.5 (m, 2H), 1.2 (d, 6H), 0.9 (t, 3H). |

1) compound number according to Table 1

II Preparation of the aminobenzoylsulfamic acid amides of the formula IIA (intermediates IIA.1):

IIa Reduction of the Nitro Group Using Iron Powder In Acetic Acid

EXAMPLE 25

N-(5-Amino-2-chloro-4-fluorobenzoyl)-N'-allyl-N'-n-propylsulfamide (IIA.1-a.241)

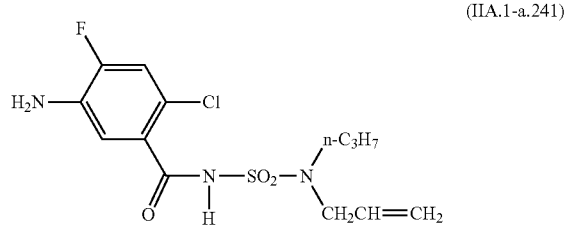

(IIA.1-a.241)

With stirring, a solution of 17.1 g (45.02 mmol) of the compound VA.1-a.241 from Example 1 in a mixture of 5 ml of tetrahydrofuran and 40 ml of acetic acid was added at 70 to 75° C. over a period of 25 minutes to a suspension of 7.54 g (135.072 mmol) of iron powder in 60 ml of acetic acid. The mixture was stirred at 70 to 75° C. for another hour and then allowed to cool and concentrated under reduced pressure. The residue was stirred with ethyl acetate and filtered, and the precipitate was washed with ethyl acetate. The filtrate was stirred with activated carbon and magnesium sulfate, filtered, washed and concentrated. The residue was turned into a paste using ethyl acetate, triturated with pentane, filtered off with suction and dried, giving 12.1 g (75.3% of theory) of the title compound of melting point 104-106° C.

IIb Catalytic Hydrogenation of the Nitro Group

EXAMPLE 31

N-(5-Amino-2-chloro-4-fluorobenzoyl)-N'-methyl-N'-isopropylsulfamide (IIA.1-a.86)

(IIA.1-a.86)

[Structure: 4-fluoro-5-amino-2-chloro benzoyl-N(H)-SO2-N(CH3)(i-C3H7)]

112.0 g (0.317 mol) of the compound VA.1-a.86 from Example 7 and 100 g of Raney nickel in 1200 ml of methanol were initially charged in a hydrogenation apparatus. With stirring, the apparatus was flushed with 10 l of nitrogen and with 10 l of hydrogen. With stirring, the mixture was hydrogenated at 22-26° C. using a hydrogen pressure of 0.1 bar. In total, 21.3 l of hydrogen were taken up. The mixture was vented and again flushed with 10 l of nitrogen. The reaction mixture was filtered off with suction through silica gel and the filtrate was concentrated under reduced pressure. This gave 100.5 g (97% of theory) of the title compound of melting point 160-162° C. (purity according to HPLC: 99.1%).

Starting with the nitrobenzoylsulfamic acid amides VA.1 listed in Table 2, the intermediates IIA (compounds of the formula II where Ar=Ar-1 where $R^b$, $R^d$=H and $R^1$ and $R^2$ have the meanings given in Table 1) of Example 26 to Example 48 listed in Table 3 were obtained in an analogous manner.

TABLE 3

IIA.1

[Structure: Rc-substituted, 5-amino benzene with Ra, C(=O)-N(H)-SO2-N(R1)(R2)]

| Example/ No.[1) | $R^c$ | $R^a$ | $R^1$ | $R^2$ | m.p. [°C.]/ $^1$H-NMR (400 MHz, CDCl$_3$) δ (ppm) |
|---|---|---|---|---|---|
| 25 IIA.1-a.241 | F | Cl | n-C$_3$H$_7$ | CH$_2$=CH—CH$_2$ | 104-106 |

TABLE 3-continued

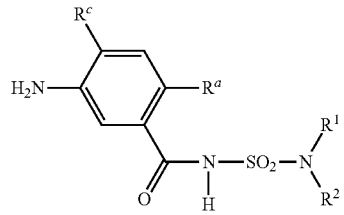

IIA.1

| Example/No.[1] | $R^c$ | $R^a$ | $R^1$ | $R^2$ | m.p. [° C.]/ $^1$H-NMR (400 MHz, CDCl$_3$) δ (ppm) |
|---|---|---|---|---|---|
| 26 IIA.1-a.492 | F | Cl | CH$_2$—CH$_2$—CH(CH$_3$)—CH$_2$—CH$_2$ | | 144-145 |
| 27 IIA.1-a.387 | F | Cl | i-C$_3$H$_7$ | HC≡C—CH$_2$ | 153-154 |
| 28 IIA.1-b.492 | H | Cl | CH$_2$—CH$_2$—CH(CH$_3$)—CH$_2$—CH$_2$ | | 139 |
| 29 IIA.1-b.241 | H | Cl | n-C$_3$H$_7$ | CH$_2$=CH—CH$_2$ | 138 |
| 30 IIA.1-b.387 | H | Cl | i-C$_3$H$_7$ | HC≡C—CH$_2$ | 139-140 |
| 31 IIA.1-a.86 | F | Cl | CH$_3$ | i-C$_3$H$_7$ | 160-162 |
| 32 IIA.1-a.76 | F | Cl | CH$_3$ | CH$_3$ | |
| 33 IIA.1-a.77 | F | Cl | CH$_3$ | C$_2$H$_5$ | |
| 34 IIA.1-a.84 | F | Cl | CH$_3$ | n-C$_3$H$_7$ | |
| 35 IIA.1-a.98 | F | Cl | CH$_3$ | c-C$_3$H$_5$ | |
| 36 IIA.1-a.85 | F | Cl | CH$_3$ | n-C$_4$H$_9$ | |
| 37 IIA.1-a.88 | F | Cl | CH$_3$ | i-C$_4$H$_9$ | |
| 38 IIA.1-a.87 | F | Cl | CH$_3$ | sek.-C$_4$H$_9$ | |
| 39 IIA.1-a.89 | F | Cl | CH$_3$ | tert.-C$_4$H$_9$ | |
| 40 IIA.1-a.93 | F | Cl | CH$_3$ | CH$_2$=CH—CH$_2$ | |
| 41 IIA.1-a.96 | F | Cl | CH$_3$ | HC≡C—CH$_2$ | |
| 42 IIA.1-a.107 | F | Cl | CH$_3$ | C$_6$H$_5$ | |
| 43 IIA.1-a.445 | F | Cl | CH$_3$ | Cyclohexyl | |
| 44 IIA.1-a.181 | F | Cl | C$_2$H$_5$ | C$_6$H$_5$ | |
| 45 IIA.1-a.446 | F | Cl | C$_2$H$_5$ | Cyclohexyl | |
| 46 IIA.1-a.160 | F | Cl | C$_2$H$_5$ | i-C$_3$H$_7$ | |
| 47 IIA.1-a.167 | F | Cl | C$_2$H$_5$ | CH$_2$=CH—CH$_2$ | |
| 48 IIA.1-b.87 | H | Cl | CH$_3$ | sek.-C$_4$H$_9$ | 8.8 (br. s), 7.2 (d, 1H), 7.1 (m, 1H), 6.8 (d, 1H), 4.0 (m, 1H), 3.8 (br. s, 2H), 2.9 (s, 3H), 1.6-1.4 (m, 2H), 1.2 (d, 3H), 0.9 (t, 3H) |

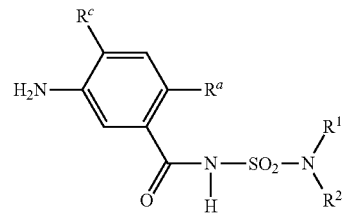

1) compound number according to Table 1

III Preparation of the phenyl iso(thio)cyanates I

EXAMPLE 109

N-(2-Chloro-4-fluoro-5-isocyanatobenzoyl)-N'-allyl-N'-n-propyl-sulfamide (IA.1-a.241)

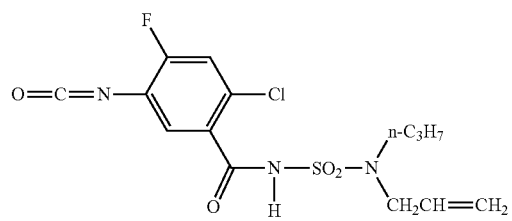

(IA.1-a.241)

With stirring at 15 to 25° C., 4.7 ml of a 4 M solution of HCl in dioxane (corresponds to 18.9 mmol of hydrogen chloride) was added to 6.0 g (17.2 mmol) of the compound IIA.1-a.241 from Example 25 in 50 ml of dioxane. The mixture was stirred at 22° C. for another hour. With stirring and slowly increasing the temperature to 95° C., 3.4 g (34.3 mmol) of phosgene were introduced over a period of 1 h. Unreacted phosgene was flushed out with nitrogen. The reaction mixture was then concentrated under reduced pressure, the residue was triturated with pentane and the supernatant was decanted off and concentrated under reduced pressure. This gave 6.5 g (95.8% of theory, purity according to $^1$H-NMR: 95%) of the title compound of melting point 85-95° C. (decomp.). IR (KBr): N=C=O 2265 cm$^{-1}$; C=O 1724 cm$^{-1}$.

EXAMPLE 94

N-(2-Chloro-4-fluoro-5-isocyanatobenzoyl)-N'-methyl-N'-isopropyl-sulfamide (IA.1-a.86)

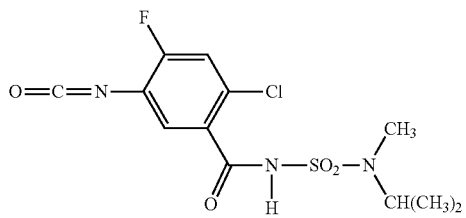
(IA.1-a.86)

A) by reaction with phosgene

At 22° C. and with stirring, phosgene was introduced into a solution of 5.0 g (15.4 mmol) of the compound IIA.1-a.86 from Example 31 in 50 ml of dioxane. Over a period of 20 minutes, the temperature was increased to the reflux temperature of the solvent mixture. Phosgene was introduced for another hour and the mixture was then allowed to cool to room temperature and flushed with nitrogen. The reaction mixture was then concentrated under reduced pressure, initially at 22° C. and then at 70° C. The residue was triturated with n-hexane, the n-hexane was decanted and the residue was dried at 70° C., giving 5.5 g (99.8% of theory of a $^1$H-NMR purity of 98%) of the title compound of melting point 146-149° C.

B) by reaction with diphosgene

With stirring at 10° C., 6.11 g (30.9 mmol) of diphosgene were added dropwise to a solution of 5.0 g (15.4 mmol) of the compound IIA.1-a.86 in 50 ml of dioxane. The reaction mixture was allowed to warm to 22° C., and stirring was continued for a further 1.5 hours. According to thin-layer chromatography, the reaction was then complete. The mixture was stirred overnight and then flushed with nitrogen and worked-up as described above in Example 94A. This gave 5.5 g (99.8% of theory of a $^1$H-NMR purity of 98%) of the title compound of melting point 148-150° C.

EXAMPLE 118

N-(2-Chloro-4-fluoro-5-isocyanatobenzoyl)-N-(4-methylpiperidine-sulfonamide) (IA.1-a.492)

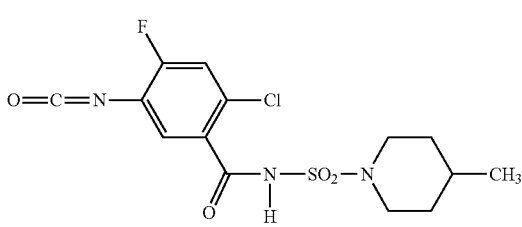
(IA.1-a.492)

With stirring at 20 to 25° C., 2.6 ml of a 4 M HCl solution (corresponds to 0.38 g (10.3 mmol) of hydrogen chloride) in dioxane were added to 1.8 g (5.1 mmol) of the compound IIA.1-a.492 from Example 26 in 50 ml of dioxane. The mixture was stirred at 22° C. for another hour. A further 1.12 g (5.66 mmol) of diphosgene were then added with stirring, and the mixture was stirred at 22° C. for 30 min., heated slowly to 95° C. and stirred for another hour. After cooling to room temperature, the mixture was concentrated under reduced pressure, the residue was triturated with pentane, the supernatant solution was decanted and the solution was reconcentrated under reduced pressure. This gave 2.0 g (98.3% of theory, of a $^1$H-NMR purity 95%) of the title compound of melting point 122-124° C. (decomp.), 135° C. clear. IR (KBr): N=C=O 2246 cm$^{-1}$; C=O 1697 cm$^{-1}$.

EXAMPLE 193

N-(2-Chloro-4-fluoro-5-isothiocyanatobenzoyl)-N'-allyl-N'-n-propyl-sulfamide (IA.1-g.241)

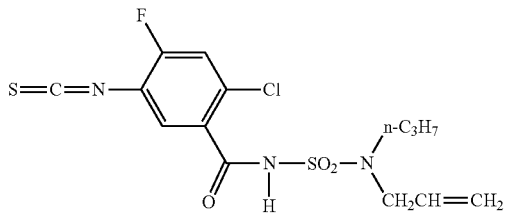
(IIA.1-g.241)

With stirring at 22° C., 1.1 g (9.4 mmol) of thiophosgene were added to 3.0 g (8.6 mmol) of the compound IIA.1-a.241 from Example 25 in 50 ml of ethyl acetate, and the mixture was then stirred for another hour and then heated at 75° C. and stirred for another hour. After concentration under reduced pressure, the residue was triturated with pentane, filtered off with suction and dried, giving 3.4 g (96.1% of theory, purity according to $^1$H-NMR 95%) of the title compound of melting point 83-85° C.

IR (KBr): N=C=S 2030 cm$^{-1}$, C=O 1725 curl.

Starting with the aminobenzoylsulfamic acid amides IA.1 listed in Table 3, the title compounds IA.1 (compounds of the formula I where Ar=Ar-1 where R$^b$, R$^d$=H and R$^1$ and R$^2$ have the meanings given in Table 1) of Example 49 to Example 216 listed in Table 4 were obtained in an analogous manner.

TABLE 4

(IA.1)

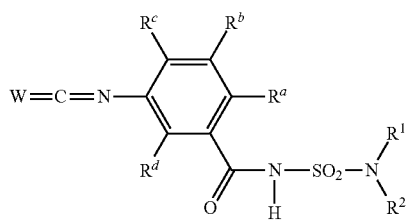

| Ex. | W | R$^c$ | R$^a$ | R$^1$ | R$^2$ | m.p. [° C.] |
|---|---|---|---|---|---|---|
| 49 | O | H | Cl | CH$_3$ | CH$_3$ | |
| 50 | O | H | Cl | CH$_3$ | C$_2$H$_5$ | |
| 51 | O | H | Cl | CH$_3$ | n-C$_3$H$_7$ | |
| 52 | O | H | Cl | CH$_3$ | i-C$_3$H$_7$ | |

TABLE 4-continued (IA.1)

| Ex. | W | $R^c$ | $R^a$ | $R^1$ | $R^2$ | m.p. [° C.] |
|---|---|---|---|---|---|---|
| 53 | O | H | Cl | $CH_3$ | $c\text{-}C_3H_5$ | |
| 54 | O | H | Cl | $CH_3$ | $n\text{-}C_4H_9$ | |
| 55 | O | H | Cl | $CH_3$ | $i\text{-}C_4H_9$ | |
| 56 | O | H | Cl | $CH_3$ | $sec.\text{-}C_4H_9$ | |
| 57 | O | H | Cl | $CH_3$ | $tert.\text{-}C_4H_9$ | |
| 58 | O | H | Cl | $C_2H_5$ | $C_2H_5$ | |
| 59 | O | H | Cl | $C_2H_5$ | $n\text{-}C_3H_7$ | |
| 60 | O | H | Cl | $C_2H_5$ | $i\text{-}C_3H_7$ | |
| 61 | O | H | Cl | $C_2H_5$ | $c\text{-}C_3H_5$ | |
| 62 | O | H | Cl | $C_2H_5$ | $n\text{-}C_4H_9$ | |
| 63 | O | H | Cl | $C_2H_5$ | $i\text{-}C_4H_9$ | |
| 64 | O | H | Cl | $C_2H_5$ | $sec.\text{-}C_4H_9$ | |
| 65 | O | H | Cl | $CH_2=CH-CH_2$ | $CH_3$ | |
| 66 | O | H | Cl | $CH_2=CH-CH_2$ | $C_2H_5$ | |
| 67 | O | H | Cl | $CH_2=CH-CH_2$ | $n\text{-}C_3H_7$ | 102-104 (Zers.) |
| 68 | O | H | Cl | $CH_2=CH-CH_2$ | $i\text{-}C_3H_7$ | |
| 69 | O | H | Cl | $CH_2=CH-CH_2$ | $n\text{-}C_4H_9$ | |
| 70 | O | H | Cl | $CH_2=CH-CH_2$ | $sec.\text{-}C_4H_9$ | |
| 71 | O | H | Cl | $HC\equiv C-CH_2$ | $CH_3$ | |
| 72 | O | H | Cl | $HC\equiv C-CH_2$ | $C_2H_5$ | |
| 73 | O | H | Cl | $HC\equiv C-CH_2$ | $n\text{-}C_3H_7$ | |
| 74 | O | H | Cl | $HC\equiv C-CH_2$ | $i\text{-}C_3H_7$ | 133-141 (Zers.) |
| 75 | O | H | Cl | $HC\equiv C-CH_2$ | $n\text{-}C_4H_9$ | |
| 76 | O | H | Cl | $CH_2-CH_2-CH(CH_3)-CH_2-CH_2$ | | 110-115 (Zers.) |
| 77 | O | H | Cl | $CH_3$ | cyclohexyl | |
| 78 | O | H | Cl | $CH_3$ | $C_6H_5$ | |
| 79 | O | H | Cl | $C_2H_5$ | cyclohexyl | |
| 80 | O | H | Cl | $C_2H_5$ | $C_6H_5$ | |
| 81 | O | H | Cl | $[CH_2]_4$ | | |
| 82 | O | H | Cl | $[CH_2]_5$ | | |
| 83 | O | H | CN | $CH_3$ | $CH_3$ | |
| 84 | O | H | CN | $CH_3$ | $C_2H_5$ | |
| 85 | O | H | CN | $CH_3$ | $i\text{-}C_3H_7$ | |
| 86 | O | H | CN | $CH_3$ | $n\text{-}C_3H_7$ | |
| 87 | O | H | CN | $CH_3$ | $i\text{-}C_4H_9$ | |
| 88 | O | H | CN | $CH_3$ | $sec.\text{-}C_4H_9$ | |
| 89 | O | H | CN | $CH_3$ | cyclohexyl | |
| 90 | O | H | CN | $CH_3$ | $C_6H_5$ | |
| 91 | O | F | Cl | $CH_3$ | $CH_3$ | |
| 92 | O | F | Cl | $CH_3$ | $C_2H_5$ | |
| 93 | O | F | Cl | $CH_3$ | $n\text{-}C_3H_7$ | |
| 94 | O | F | Cl | $CH_3$ | $i\text{-}C_3H_7$ | 144-148 |
| 95 | O | F | Cl | $CH_3$ | $c\text{-}C_3H_5$ | |
| 96 | O | F | Cl | $CH_3$ | $n\text{-}C_4H_9$ | |
| 97 | O | F | Cl | $CH_3$ | $i\text{-}C_4H_9$ | |
| 98 | O | F | Cl | $CH_3$ | $sec.\text{-}C_4H_9$ | |
| 99 | O | F | Cl | $CH_3$ | $tert.\text{-}C_4H_9$ | |
| 100 | O | F | Cl | $C_2H_5$ | $C_2H_5$ | |
| 101 | O | F | Cl | $C_2H_5$ | $n\text{-}C_3H_7$ | |
| 102 | O | F | Cl | $C_2H_5$ | $i\text{-}C_3H_7$ | |
| 103 | O | F | Cl | $C_2H_5$ | $c\text{-}C_3H_5$ | |
| 104 | O | F | Cl | $C_2H_5$ | $n\text{-}C_4H_9$ | |
| 105 | O | F | Cl | $C_2H_5$ | $i\text{-}C_4H_9$ | |
| 106 | O | F | Cl | $C_2H_5$ | $sec.\text{-}C_4H_9$ | |
| 107 | O | F | Cl | $CH_2=CH-CH_2$ | $CH_3$ | |
| 108 | O | F | Cl | $CH_2=CH-CH_2$ | $C_2H_5$ | |
| 109 | O | F | Cl | $CH_2=CH-CH_2$ | $n\text{-}C_3H_7$ | 85-95 (Zers.) |
| 110 | O | F | Cl | $CH_2=CH-CH_2$ | $i\text{-}C_3H_7$ | |
| 111 | O | F | Cl | $CH_2=CH-CH_2$ | $n\text{-}C_4H_9$ | |
| 112 | O | F | Cl | $CH_2=CH-CH_2$ | $sec.\text{-}C_4H_9$ | |
| 113 | O | F | Cl | $HC\equiv C-CH_2$ | $CH_3$ | |
| 114 | O | F | Cl | $HC\equiv C-CH_2$ | $C_2H_5$ | |
| 115 | O | F | Cl | $HC\equiv C-CH_2$ | $n\text{-}C_3H_7$ | |
| 116 | O | F | Cl | $HC\equiv C-CH_2$ | $i\text{-}C_3H_7$ | 124-126 (Zers.) |
| 117 | O | F | Cl | $HC\equiv C-CH_2$ | $n\text{-}C_4H_9$ | |
| 118 | O | F | Cl | $CH_2-CH_2-CH(CH_3)-CH_2-CH_2$ | | 122-124 (Zers.) |
| 119 | O | F | Cl | $CH_3$ | cyclohexyl | |
| 120 | O | F | Cl | $CH_3$ | $C_6H_5$ | |
| 121 | O | F | Cl | $C_2H_5$ | cyclohexyl | |
| 122 | O | F | Cl | $C_2H_5$ | $C_6H_5$ | |
| 123 | O | F | Cl | $[CH_2]_4$ | | |
| 124 | O | F | Cl | $[CH_2]_5$ | | |
| 125 | O | F | CN | $CH_3$ | $CH_3$ | |
| 126 | O | F | CN | $CH_3$ | $C_2H_5$ | |
| 127 | O | F | CN | $CH_3$ | $i\text{-}C_3H_7$ | |
| 128 | O | F | CN | $CH_3$ | $n\text{-}C_3H_7$ | |
| 129 | O | F | CN | $CH_3$ | $i\text{-}C_4H_9$ | |
| 130 | O | F | CN | $CH_3$ | $sec.\text{-}C_4H_9$ | |
| 131 | O | F | CN | $CH_3$ | cyclohexyl | |
| 132 | O | F | CN | $CH_3$ | $C_6H_5$ | |
| 133 | S | H | Cl | $CH_3$ | $CH_3$ | |
| 134 | S | H | Cl | $CH_3$ | $C_2H_5$ | |
| 135 | S | H | Cl | $CH_3$ | $n\text{-}C_3H_7$ | |
| 136 | S | H | Cl | $CH_3$ | $i\text{-}C_3H_7$ | |
| 137 | S | H | Cl | $CH_3$ | $c\text{-}C_3H_5$ | |
| 138 | S | H | Cl | $CH_3$ | $n\text{-}C_4H_9$ | |
| 139 | S | H | Cl | $CH_3$ | $i\text{-}C_4H_9$ | |
| 140 | S | H | Cl | $CH_3$ | $sec.\text{-}C_4H_9$ | |
| 141 | S | H | Cl | $CH_3$ | $tert.\text{-}C_4H_9$ | |
| 142 | S | H | Cl | $C_2H_5$ | $C_2H_5$ | |
| 143 | S | H | Cl | $C_2H_5$ | $n\text{-}C_3H_7$ | |
| 144 | S | H | Cl | $C_2H_5$ | $i\text{-}C_3H_7$ | |
| 145 | S | H | Cl | $C_2H_5$ | $c\text{-}C_3H_5$ | |
| 146 | S | H | Cl | $C_2H_5$ | $n\text{-}C_4H_9$ | |
| 147 | S | H | Cl | $C_2H_5$ | $i\text{-}C_4H_9$ | |
| 148 | S | H | Cl | $C_2H_5$ | $sec.\text{-}C_4H_9$ | |
| 149 | S | H | Cl | $CH_2=CH-CH_2$ | $CH_3$ | |
| 150 | S | H | Cl | $CH_2=CH-CH_2$ | $C_2H_5$ | |
| 151 | S | H | Cl | $CH_2=CH-CH_2$ | $n\text{-}C_3H_7$ | 99-100 |
| 152 | S | H | Cl | $CH_2=CH-CH_2$ | $i\text{-}C_3H_7$ | |
| 153 | S | H | Cl | $CH_2=CH-CH_2$ | $n\text{-}C_4H_9$ | |
| 154 | S | H | Cl | $CH_2=CH-CH_2$ | $sec.\text{-}C_4H_9$ | |
| 155 | S | H | Cl | $HC\equiv C-CH_2$ | $CH_3$ | |
| 156 | S | H | Cl | $HC\equiv C-CH_2$ | $C_2H_5$ | |
| 157 | S | H | Cl | $HC\equiv C-CH_2$ | $n\text{-}C_3H_7$ | |
| 158 | S | H | Cl | $HC\equiv C-CH_2$ | $i\text{-}C_3H_7$ | 163-164 |
| 159 | S | H | Cl | $HC\equiv C-CH_2$ | $n\text{-}C_4H_9$ | |
| 160 | S | H | Cl | $CH_2-CH_2-CH(CH_3)-CH_2-CH_2$ | | 143-144 |
| 161 | S | H | Cl | $CH_3$ | cyclohexyl | |
| 162 | S | H | Cl | $CH_3$ | $C_6H_5$ | |
| 163 | S | H | Cl | $C_2H_5$ | cyclohexyl | |
| 164 | S | H | Cl | $C_2H_5$ | $C_6H_5$ | |
| 165 | S | H | Cl | $[CH_2]_4$ | | |
| 166 | S | H | Cl | $[CH_2]_5$ | | |
| 167 | S | H | CN | $CH_3$ | $CH_3$ | |
| 168 | S | H | CN | $CH_3$ | $C_2H_5$ | |
| 169 | S | H | CN | $CH_3$ | $i\text{-}C_3H_7$ | |
| 170 | S | H | CN | $CH_3$ | $n\text{-}C_3H_7$ | |
| 171 | S | H | CN | $CH_3$ | $i\text{-}C_4H_9$ | |
| 172 | S | H | CN | $CH_3$ | $sec.\text{-}C_4H_9$ | |
| 173 | S | H | CN | $CH_3$ | cyclohexyl | |
| 174 | S | H | CN | $CH_3$ | $C_6H_5$ | |
| 175 | S | F | Cl | $CH_3$ | $CH_3$ | |
| 176 | S | F | Cl | $CH_3$ | $C_2H_5$ | |

TABLE 4-continued (IA.1)

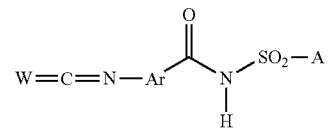

| Ex. | W | $R^c$ | $R^a$ | $R^1$ | $R^2$ | m.p. [° C.] |
|---|---|---|---|---|---|---|
| 177 | S | F | Cl | CH$_3$ | n-C$_3$H$_7$ | |
| 178 | S | F | Cl | CH$_3$ | i-C$_3$H$_7$ | |
| 179 | S | F | Cl | CH$_3$ | c-C$_3$H$_5$ | |
| 180 | S | F | Cl | CH$_3$ | n-C$_4$H$_9$ | |
| 181 | S | F | Cl | CH$_3$ | i-C$_4$H$_9$ | |
| 182 | S | F | Cl | CH$_3$ | sec.-C$_4$H$_9$ | |
| 183 | S | F | Cl | CH$_3$ | tert.-C$_4$H$_9$ | |
| 184 | S | F | Cl | C$_2$H$_5$ | C$_2$H$_5$ | |
| 185 | S | F | Cl | C$_2$H$_5$ | n-C$_3$H$_7$ | |
| 186 | S | F | Cl | C$_2$H$_5$ | i-C$_3$H$_7$ | |
| 187 | S | F | Cl | C$_2$H$_5$ | c-C$_3$H$_5$ | |
| 188 | S | F | Cl | C$_2$H$_5$ | n-C$_4$H$_9$ | |
| 189 | S | F | Cl | C$_2$H$_5$ | i-C$_4$H$_9$ | |
| 190 | S | F | Cl | C$_2$H$_5$ | sec.-C$_4$H$_9$ | |
| 191 | S | F | Cl | CH$_2$=CH—CH$_2$ | CH$_3$ | |
| 192 | S | F | Cl | CH$_2$=CH—CH$_2$ | C$_2$H$_5$ | |
| 193 | S | F | Cl | CH$_2$=CH—CH$_2$ | n-C$_3$H$_7$ | 83-85 |
| 194 | S | F | Cl | CH$_2$=CH—CH$_2$ | i-C$_3$H$_7$ | |
| 195 | S | F | Cl | CH$_2$=CH—CH$_2$ | n-C$_4$H$_9$ | |
| 196 | S | F | Cl | CH$_2$=CH—CH$_2$ | sec.-C$_4$H$_9$ | |
| 197 | S | F | Cl | HC≡C—CH$_2$ | CH$_3$ | |
| 198 | S | F | Cl | HC≡C—CH$_2$ | C$_2$H$_5$ | |
| 199 | S | F | Cl | HC≡C—CH$_2$ | n-C$_3$H$_7$ | |
| 200 | S | F | Cl | HC≡C—CH$_2$ | i-C$_3$H$_7$ | 155-156 |
| 201 | S | F | Cl | HC≡C—CH$_2$ | n-C$_4$H$_9$ | |
| 202 | S | F | Cl | CH$_2$—CH$_2$—CH(CH$_3$)—CH$_2$—CH$_2$ | | 152-153 |
| 203 | S | F | Cl | CH$_3$ | cyclohexyl | |
| 204 | S | F | Cl | CH$_3$ | C$_6$H$_5$ | |
| 205 | S | F | Cl | C$_2$H$_5$ | cyclohexyl | |
| 206 | S | F | Cl | C$_2$H$_5$ | C$_6$H$_5$ | |
| 207 | S | F | Cl | [CH$_2$]$_4$ | | |
| 208 | S | F | Cl | [CH$_2$]$_5$ | | |
| 209 | S | F | CN | CH$_3$ | CH$_3$ | |
| 210 | S | F | CN | CH$_3$ | C$_2$H$_5$ | |
| 211 | S | F | CN | CH$_3$ | i-C$_3$H$_7$ | |
| 212 | S | F | CN | CH$_3$ | n-C$_3$H$_7$ | |
| 213 | S | F | CN | CH$_3$ | i-C$_4$H$_9$ | |
| 214 | S | F | CN | CH$_3$ | sec.-C$_4$H$_9$ | |
| 215 | S | F | CN | CH$_3$ | cyclohexyl | |
| 216 | S | F | CN | CH$_3$ | C$_6$H$_5$ | |

EXAMPLE 217

8-(5'-N-Isopropyl-N-methylsulfamoyl-carboxamido-4'-chloro-2'-fluorophenyl)-4-oxo-7,9-dioxo-1,2,8-triaza[4.3.0]nonane (Example 146 of WO 01/83459)

217.1: Methyl tetrahydro-N-(4-chloro-2-fluoro-5-N-isopropyl-N-methylsulfamoylcarboxamidophenyl)-4H-1,3,4-oxadiazine-3-carboxamide-4-carboxylate Over a period of 5 minutes, 9.8 g (10.1 mmol) of methyl tetrahydro-4H-1,3,4-oxadiazine-4-carboxylate, as a 15% strength solution in 1,2-dichloroethane, were added at 22° C. and with stirring to a mixture of 3.5 g (10.1 mmol) of N-(2-chloro-4-fluoro-5-isocyanatobenzoyl)-N'-isopropyl-N'-methylsulfamide IA-a.86 from Example 94 in 100 ml of 1,2-dichloroethane, and the mixture was stirred for 18 hours. The reaction mixture was then purified by flash chromatography on silica gel using 200 ml portions of a mixture of methylene chloride/diethyl ether=1:6 as mobile phase. The solvent was removed under reduced pressure, giving 4.3 g (82.3% of theory) of methyl tetrahydro-N-(4-chloro-2-fluoro-5-N-isopropyl-N-methylsulfamoylcarboxamidophenyl)-4H-1,3,4-oxadiazine-3-carboxamide-4-carboxylate of melting point 69° C. (decomposition).

217.2: 8-(5'-N-Isopropyl-N-methylsulfamoylcarboxamido-4'-chloro-2'-fluorophenyl)-4-oxo-7,9-dioxo-1,2,8-triaza[4.3.0]nonane In a reaction vessel fitted with stirrer and water separator, 0.85 g (1.7 mmol) of the compound from Example 217.1 was initially charged in 80 ml of toluene. With stirring, 0.18 g (1.8 mmol) of 97% pure sodium tert-butoxide was added at 22° C., and the mixture was then heated to reflux with stirring. The toluene was occasionally replaced. In total, the mixture was heated at reflux for 7 hours until the reaction mixture became more highly liquid and the solids were almost completely dissolved. After cooling, the reaction mixture was acidified using a 1M solution of HCl in 10 ml of diethyl ether and concentrated under reduced pressure. The residue was dissolved in methylene chloride, extracted with 1N hydrochloric acid and water, dried and concentrated under reduced pressure. This gave 0.67 g (76% of theory) of the title compound of melting point 112-118° C. Following trituration with diethyl ether, the melting point was 115-120° C.

The invention claimed is:

1. A phenyl iso(thio)cyanate of formula I,

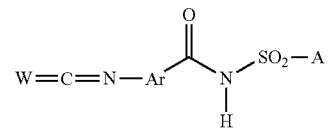

(I)

where:
W is oxygen or sulfur,
Ar is phenyl which may be mono- or polysubstituted by the following groups: hydrogen, halogen, C$_1$-C$_4$-haloalkyl or cyano, and
A is a radical derived from a primary or secondary amine or is NH$_2$, 2. A phenyl iso(thio)cyanate of formula Ia,

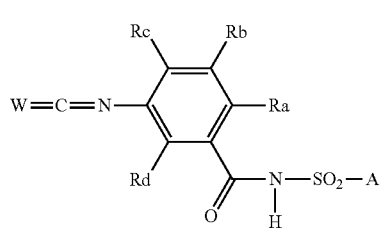

(Ia)

wherein:
W is oxygen or sulfur,
A is a radical derived from a primary or secondary amine or is NH$_2$, and
$R^a$ is fluorine, chlorine or cyano, $R^c$ is hydrogen, fluorine or chlorine and $R^b$ and $R^d$ are each hydrogen.

3. A phenyl iso(thio)cyanate of the formula Ia as defined in claim 2, wherein A is a radical of the formula NR¹R² where
R¹ and R² independently of one another represent hydrogen, $C_1$-$C_{10}$-alkyl, $C_2$-$C_{10}$-alkenyl or $C_2$-$C_{10}$-alkynyl which may be unsubstituted or substituted by one of the following radicals:

$C_1$-$C_4$-alkoxy, $C_1$-$C_4$-alkylthio, CN, NO₂, formyl, $C_1$-$C_4$-alkylcarbonyl, $C_1$-$C_4$-alkoxycarbonyl, $C_1$-$C_4$-alkylaminocarbonyl, $C_1$-$C_4$-dialkylaminocarbonyl, $C_1$-$C_4$-alkylsulfinyl, $C_1$-$C_4$-alkylsulfonyl, $C_3$-$C_{10}$-cycloalkyl, 3- to 8-membered heterocyclyl having one, two or three heteroatoms selected from the group consisting of O, S, N and a group NR⁶ (where R⁶ is hydrogen, $C_1$-$C_6$-alkyl, $C_3$-$C_6$-alkenyl or $C_3$-$C_6$-alkynyl), phenyl, which may have 1, 2, 3 or 4 substituents selected from the group consisting of halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, $C_1$-$C_3$-alkylamino, $C_1$-$C_3$-dialkylamino, formyl, nitro and cyano, $C_1$-$C_{10}$-haloalkyl, $C_2$-$C_{10}$-haloalkenyl, $C_2$-$C_{10}$-haloalkynyl, $C_3$-$C_8$-cycloalkyl, $C_3$-$C_{10}$-cycloalkenyl, 3- to 8-membered heterocyclyl having one to three heteroatoms selected from the group consisting of O, S, N and a group NR⁶, wherein R⁶ is hydrogen, $C_1$-$C_6$-alkyl, $C_3$-$C_6$-alkenyl or $C_3$-$C_6$-alkynyl), phenyl or naphthyl, where $C_3$-$C_8$-cycloalkyl, $C_3$-$C_{10}$-cycloalkenyl, 3- to 8-membered heterocyclyl, phenyl and naphthyl may have 1, 2, 3 or 4 substituents selected from the group consisting of halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, $C_1$-$C_3$-alkylamino, $C_1$-$C_3$-dialkylamino, phenoxy, nitro and cyano, or R¹ and R² together with the nitrogen atom to which they are attached form a saturated or partially unsaturated 5- to 8-membered nitrogen heterocycle which may be substituted by $C_{1i}$-$C_4$-alkyl, $C_1$-$C_4$-alkoxy and/or $C_1$-$C_4$-haloalkyl and may have one or two carbonyl groups, thiocarbonyl groups and/or one or two further heteroatoms selected from the group consisting of O, S, N and a group NR⁶, wherein R⁶ is as defined above, as ring members.

4. A phenyl iso(thio)cyanate of formula Ia in claim 3, wherein R¹ and R² independently of one another are hydrogen, $C_1$-$C_6$-alkyl which is optionally substituted by a substituent selected from the group consisting of halogen, cyano, $C_1$-$C_4$-alkoxy, $C_1$-$C_4$-alkoxycarbonyl, $C_1$-$C_4$-alkylthio, $C_3$-$C_8$-cycloalkyl, furyl, thienyl, 1,3-dioxolanyl, phenyl which for its part is optionally substituted by halogen or $C_1$-$C_4$-alkoxy, $C_2$-$C_6$-alkenyl, $C_2$-$C_6$- alkynyl, $C_3$-$C_8$-cycloalkyl or phenyl which is optionally substituted by 1 or 2 substituents selected from the group consisting of halogen, $C_1$-$C_4$-alkyl, $C_1$-$C_4$-fluoroalkyl, $C_1$-$C_4$-alkoxy, $C_1$-$C_4$-alkoxycarbonyl, nitro and $C_1$-$C_3$-dialkylamino, naphthyl or pyridyl or R¹ and R² together with the nitrogen atom to which they are attached form a five-, six-or seven-membered saturated or unsaturated nitrogen heterocycle which may optionally contain a further heteroatom selected from the group consisting of N, a group NR⁶ (where R⁶ is as defined above) and O as ring member and/or which may be substituted by one, two or three substituents selected from the group consisting of $C_1$-$C_4$-alkyl and $C_4$-$C_4$-haloalkyl.

5. A process for preparing the phenyl iso(thio)cyanate of claim 1 which comprises reacting a compound of formula II,

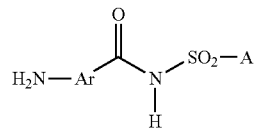

(II)

where the variables Ar and A are as defined above or its HCl adduct, with phosgene, thiophosgene or diphosgene.

6. The process of claim 5, wherein the HCl adduct of the compound of formula II is used.

7. The process of claim 5, wherein from 0.9 to 2 molar equivalents of phosgene, thiophosgene or diphosgene are used, based on the moles of the compound of formula II.

8. The process of claim 5, wherein the reaction of the HCl adduct of the compound of formula II is carried out in the presence of activated carbon.

9. A process for preparing the phenyl iso(thio)cyanate of claim 2, wherein a compound of the formula IIa

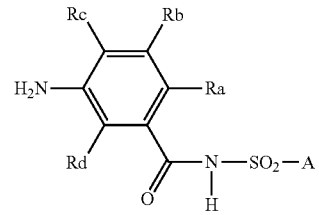

(IIa)

wherein:
$R^a$, $R^b$, $R^c$ and $R^d$ independently of one another are hydrogen, halogen, $C_1$-$C_4$-haloalkyl or cyano, and
A is a radical derived from a primary or secondary amine or is NH₂
or its HCl adduct is reacted with phosgene, thiophosgene or diphosgene, giving a compound of the formula Ia

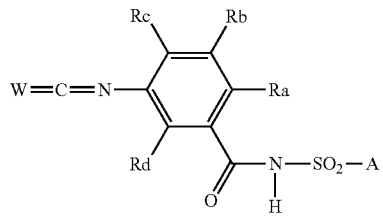

(Ia)

where the variables $R^a$, $R^b$, $R^c$, $R^d$, A are as defined above and W is oxygen or sulfur.

10. The process of claim 5, wherein the radical A in formula I is NR¹R²,
where:
R¹ and R² independently of one another represent hydrogen, $C_1$-$C_{10}$-alkyl, $C_2$-$C_{10}$-alkenyl or $C_2$-$C_{10}$-alkynyl which may be unsubstituted or substituted by one of the following radicals: $C_1$-$C_4$-alkoxy, $C_1$-$C_4$-alkylthio, CN, NO₂, formyl, $C_1$-$C_4$-alkylcarbonyl, $C_1$-$C_4$-alkoxycarbonyl $C_1$-$C_4$-alkylaminocarbonyl, $C_1$-$C_4$-dialkylaminocarbonyl, $C_1$-$C_4$-alkylsulfinyl $C_1$-$C_4$-alkylsulfonyl, $C_3$-$C_{10}$-cycloalkyl, 3- to 8-membered heterocyclyl having one, two or three heteroatoms selected from the group consisting of O, S, N and a group NR⁶(where R⁶ is hydrogen, $C_1$-$C_6$-alkyl, $C_3$-$C_6$-alkenyl or $C_3$-$C_6$-alkynyl), phenyl, which may have 1, 2, 3 or 4 substituents selected from the group consisting of halogen, $C_1$-$C_4$-alkyl, $C_1$-$C_{4\text{-alkoxy}}$, $C_1$-$C_4$-fluoroalkyl, $C_1$-$C_4$-alkyloxycarbonyl, trifluoromethylsulfonyl, $C_1$-$C_3$-alkylamino, $C_1$-$C_3$-dialkylamino, formyl, nitro and cyano, $C_0$-$C_{10}$-haloalkyl, $C_2$-$C_{10}$-haloalkenyl, $C_2$-$C_{10}$-haloalkynyl, $C_3$-$C_8$-cycloalkyl, $C_3$-$C_{10}$-cycloalkenyl, 3- to 8-membered heterocyclyl having one to three heteroatoms selected from the group consisting of O, S, N and a group $NR^6$ (where $R^6$ is hydrogen, $C_1$-$C_6$-alkyl, $C_3$-$C_6$-alkenyl or $C_3$-$C_6$-alkynyl), phenyl or naphthyl, wherein the $C_3$-$C_8$-cycloalkyl, $C_3$-$C_{10}$-cycloalkenyl, 3- to 8-membered heterocyclyl, phenyl and naphthyl may have 1, 2, 3 or 4 substituents selected from the group consisting of halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, $C_1$-$C_3$-alkylamino, $C_1$-$C_3$-dialkylamino, phenoxy, nitro and cyano, or $R^1$ and $R^2$ together with the nitrogen atom to which they are attached form a saturated or partially unsaturated 5- to 8-membered nitrogen heterocycle which may be substituted by $C_1$-$C_4$-alkyl, $C_1$-$C_4$-alkoxy and/or $C_1$-$C_4$-haloalkyl and may have one or two carbonyl groups, thiocarbonyl groups and/or one or two further heteroatoms selected from the group consisting of O, S, N and a group $NR^6$, wherein $R^6$ is as defined above, as ring members.

11. The process of claim 5, wherein the compound of formula II is prepared by the following steps:
i) reacting an aroyl compound of the formula III

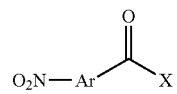

(III)

in which the variable Ar is as defined above and X is halogen, OH or $C_1$-$C_4$-alkoxy with a sulfamic acid amide of the formula IV,

(IV)

where A is as defined above and
ii) reducing N-aroylsulfamic acid amide, obtained in step (i), of the formula V

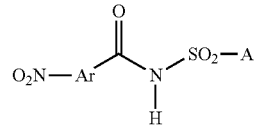

(V)

where Ar and A are as defined above, giving a compound of the formula II.

12. The process of claim 11, wherein in step (ii) the reduction is carried out in the presence of catalytic amounts of transition metals or transition metal compounds.

13. The process of claim 11, wherein in step (ii) the reduction is carried out in the presence of iron and at least one $C_1$-$C_4$-carboxylic acid.

14. A process of claim 11, wherein in step (ii) the reduction is carried out in the presence of Raney nickel and hydrogen.

\* \* \* \* \*